United States Patent
Demnitz et al.

(10) Patent No.: US 9,556,132 B2
(45) Date of Patent: Jan. 31, 2017

(54) TETRAZOLE DERIVATIVES AND THEIR USE AS POTASSIUM CHANNEL MODULATORS

(71) Applicant: SANIONA A/S, Ballerup (DK)

(72) Inventors: Joachim Demnitz, Copenhagen (DK); Susanne Jorgensen, Frederiksberg (DK)

(73) Assignee: Saniona A/S, Ballerup (DK)

( * ) Notice: Subject to any disclaimer, the term of this patent is extended or adjusted under 35 U.S.C. 154(b) by 0 days.

(21) Appl. No.: 14/411,314

(22) PCT Filed: Jun. 25, 2013

(86) PCT No.: PCT/EP2013/063321
§ 371 (c)(1),
(2) Date: May 7, 2015

(87) PCT Pub. No.: WO2014/001363
PCT Pub. Date: Jan. 3, 2014

(65) Prior Publication Data
US 2015/0203458 A1 Jul. 23, 2015

(30) Foreign Application Priority Data
Jun. 25, 2012 (DK) .................................. 2012 7035

(51) Int. Cl.
*C07D 257/04* (2006.01)
(52) U.S. Cl.
CPC .................................. *C07D 257/04* (2013.01)
(58) Field of Classification Search
None
See application file for complete search history.

(56) References Cited

U.S. PATENT DOCUMENTS 5,294,620 A * 3/1994 Ratcliffe .............. C07D 471/04
514/300

FOREIGN PATENT DOCUMENTS

| EP | 0495626 A | 7/1992 |
| EP | 0554098 A2 | 8/1993 |
| WO | WO 2009/003921 A1 | 1/2009 |

OTHER PUBLICATIONS

"Inflammatory Bowel Disease," Centers for Disease Control, <http://www.cdc.gov/ibd/>.*
Compston, A., and Coles, A., "Multiple sclerosis," The Lancet, vol. 359, pp. 1221-1231 (Apr. 6, 2002).*
Hartung, H., et al., "What do we know about the mechanism of action of disease-modifying treatments in MS?" J. Neurol., vol. 251 (suppl. 5), pp. V/12-V/29 (2004).*
Wulff et al., "Modulators of small- and -intermediate-conductance calcium-activated potassium channels and their therapeutic indications", Current Medicinal Chemistry, Jan. 2007, vol. 14, No. 13, 1437-1457.
Lundby et al., "Effect of the Ito activator NS5806 on cloned Kv4 channels depends on the accessory protein KChIP2", British Journal of Pharmacology, Aug. 2010, vol. 160, No. 8, 2028-2044.
Wulff et al., "K + Channel Modulators for the Treatment of Neurological Disorders and Autoimmune Diseases", Chemical Reviews, May 2008, vol. 108, No. 5, 1744-1773.

* cited by examiner

*Primary Examiner* — Alicia L Otton
(74) *Attorney, Agent, or Firm* — Baker & Hostetler LLP

(57) ABSTRACT

A tetrazole derivative of general formula (I), a pharmaceutical composition comprising said compound and its use for treating, alleviating or preventing diseases or disorders relating to the activity of potassium channels.

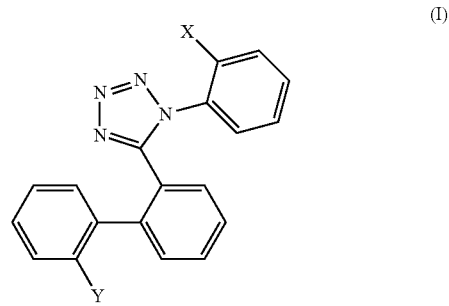

(I)

8 Claims, No Drawings

TETRAZOLE DERIVATIVES AND THEIR USE AS POTASSIUM CHANNEL MODULATORS

The present invention relates to new tetrazole derivatives, a process for Preparing the same, pharmaceutical compositions comprising such compounds and their use for treating, alleviating or preventing diseases or disorders relating to the activity of potassium channels.

Ion channels are trans-membrane proteins, which catalyse the transport of inorganic ions across cell membranes. The ion channels participate in very diverse processes among which the generation and timing of action potentials, synaptic transmissions, secretion of hormones or contraction of muscles.

All mammalian cells express potassium (K+) channels in their cell membranes, and the channels play a dominant role in the regulation of the membrane potential. In nerve and muscle cells they influence the form of the action potential, regulate the frequency and firing patterns of action potentials, the release of neurotransmitters as well as the degree of bronchodilation and vasodilation. In non-excitable cells K+ channels regulate cellular proliferation and migration as well as the secretion of cytokines.

From a molecular and functional point of view, the K+ channels represent the largest and most diverse group of ion channels. It can be divided into four broad families:
- voltage-activated K+ channels (Kv),
- inward rectifier K+ channels (KIR),
- two-pore K+ channels (K2P),
- and calcium-activated K+ channels (KCa).

In the KCa channels, two main groups can be distinguished:
- the calmodulin-dependent families, consisting of the small conductance (SK's or KCa2.x) and intermediate conductance channels (IK or KCa3.1)
- and the intracellular ligand gated families, consisting of the classic Ca2+- and voltage-activated big conductance channel (BK, KCa1.1) as well as channels sensitive to other intracellular ions (KCa4.x; and KCa5.1).

The IK channel is the only KCa channel that is expressed essentially in non-excitable cells, in particular in cells of the immune system among which T- and B-lymphocytes, macrophages, microglia cells, dendritic cells and mast cells.

It has been observed that the expression of IK channels increases in antigen stimulated cells, and that their Ca2+-dependent activation helps to keep the membrane potential negative, thereby allowing a permissive, continuous Ca2+-influx, which is probably key to clonal expansion and selective secretion of pro-inflammatory cytokines. Blocking the IK channel has been demonstrated to be an anti-inflammatory principle in animal models of autoimmune diseases, as well as asthma. It has also been observe that de-differentiation and loss of the contractile phenotype of vascular smooth muscle cells is accompanied with a switch-on of IK expression in these cells; and that blocking the channel can lead to protection against the development of atherosclerosis and restenosis. IK channel blockers have also shown beneficial effects in models of brain edema (microglia activation); diarrhoea, as well as polycystic kidney disease (epithelial IK channels).

Inflammatory disorders are characterized by their systemic effects. Inflammation is the body's response to injury, infection or molecules perceived by the immune system as foreign. Clinically, inflammation is characterized by pain, redness, heat, swelling and altered function of affected tissue. Although the ability to mount an inflammatory response is essential for survival, the ability to control inflammation is also necessary for health. Examples of chronic inflammation disorders include inflammatory bowel disease (IBD), rheumatoid arthritis (RA), multiple sclerosis (MS) and asthma.

Inflammatory bowel disease (IBD) is a chronic autoimmune disease affecting the gastrointestinal tract with symptoms of abdominal pain, vomiting, diarrhoea, hematochezia, and weight loss. IBD comes in two main forms, ulcerative colitis (UC) and Crohn's disease (CD). UC exclusively affects the colon and rectum, whereas CD may affect the entire gastrointestinal tract. Histologically UC is characterized by extended mucosal inflammation in contrast to CD, where deep punctuate lesions affect all layers of the intestinal wall. Initial stage IBD is currently treated medically by steroids such as budesonide, by aminosalicylates such as sulfasalazine or by general immunosuppressants such as azathioprine, whereas later stage severe cases often require surgery in form of colostomy. Recently, antibodies against TNF-α have also been used clinically with some success.

Rheumatoid arthritis (RA) causes chronic inflammation of the joints and inflammation of the tissue around the joints, as well as other organs in the body. While rheumatoid arthritis is a chronic illness, patients may experience long periods without symptoms. Typically, however, rheumatoid arthritis is a progressive illness that has the potential to cause joint destruction and functional disability.

Multiple sclerosis (MS) is a debilitating chronic inflammatory disease that affects the central nervous system. Current research suggests that the illness is initiated by an autoimmune malfunction, where the body incorrectly directs certain leukocytes against proteins in the protective myelin sheath surrounding nerves in the brain and spinal cord. The result is multiple areas of scarring or sclerosis. Eventually, progressive damage can obliterate the nerve signals that control muscle coordination, strength, sensation and even vision.

Asthma is a chronic inflammatory airway disease characterised by variable and recurring symptoms, reversible airflow obstruction, and bronchospasms. Symptoms include wheezing, cough, tight chest and shortness of breath.

Consequently, compounds acting as potassium channel modulating agents may be very useful in the treatment, alleviation and/or prevention of chronic inflammation disorders.

To date, different therapeutic options are available for treating, alleviating or preventing these diseases.

For inflammatory bowel disease (IBD), existing treatments allow achieving remission and maintaining patients in remission but do not allow curing said disease.

Treatments to achieve remission include steroids, which, by virtue of their well-publicised side-effects, that also include increased susceptibility to infection, do not lend themselves to long-term treatment. 5-aminosalicylic acids, such as in the form of sulphasalazine for example, are used for chronic remission maintenance treatment, the main drawback being a significant proportion of non-responders among UC patients, decreased kidney function as well as high and frequent doses, which elicit poor compliance, a major unmet need in chronic inflammatory bowel disease treatment. Biologics such as the TNF-alpha inhibitor infliximab are used for treating IBD. Their drawbacks include high cost, inconvenience of application (injections), waning of efficacy and elicitation of increased risk of infection as a result of their immunosuppressive characteristic. Immunomodulators used in inflammatory bowel disease such asazathioprine, 6-mercaptopurine and methotrexate also increase the risk for infections and for some types of cancer, as well as being liver toxic. Antibiotics such as metronidazole and ciprofloxacin are used in some patients.

First line treatment of rheumatoid arthritis (RA) is covered by disease-modifying antirheumatic drugs (DMARDs) and biologics. These help to control the disease and limit damage to the joints. A second group of drugs includes pain- and inflammation-limiting drugs such as corticosteroids, non-steroidal anti-inflammatory drugs (NSAIDS) and other pain medicines, but these drugs do not limit damage to the joints. Joint replacement and other surgical interventions can be used in advanced joint damage. DMARD treatment risks include infection liability, kidney and/or liver damage and the potential for birth defects (methotrexate, leflunomide). Women should not consider using these drugs during pregnancy without consultation of their doctor. Biologics increase infection susceptibility including tuberculosis. Some patients also show reactions at the injection site. Steroids can cause weight gain and bone loss, thus increasing the risk of osteoporosis. Similarly to biologics, steroids can also increase infection risk. They can also worsen diabetes. In view of such side effects, steroids should be avoided for chronic treatment. NSAIDs may cause stomach bleeding and some have been linked to increased heart disease risk. NSAIDs should be used with caution in people with heart, liver or kidney disease.

The aims of pharmacological therapy for multiple sclerosis (MS) are to shorten the duration of attacks or relapses, ease symptoms and slow disease progression by reducing the rate of the attacks. The types of drugs used depend upon a patient's form of MS, and include corticosteroids and immunotherapy with drugs such as teriflunomide, interferon beta-1a, glatiramer acetate, fingolimod, mitoxantrone, dimethyl fumarate and natalizumab. Although not limited to those mentioned, side-effects and/or risks associated with the abovementioned drugs are as follows: teriflunomide hepatotoxicity, risk of birth defects, peripheral neuropathy, renal failure and skin reactions; interferon beta-1a (depression and suicidal thoughts, seizures, heart problems, liver problems, allergic reactions and flu-like symptoms); glatiramer acetate (injection site reactions, flushing, chest tightness and palpitations); fingolimod (greater risk of infection, liver problems, influenza and diarrhea); mitoxantrone (cardiotoxicity, secondary acute myelogenousleukemia and infection risks); dimethyl fumarate (reduced white cell count, elevated liver enzymes, flushing and gastrointestinal problems); natalizumab (fatal progressive multifocal leukoencephalopathy and infection risk.

Asthma treatments include beta-2 agonists such as salbutamol and salmeterol, anticholinergics such as ipratropium bromide and leukotriene antagonists such as montelukast. The most effective anti-inflammatory for asthma are corticosteroids such as beclometasone.

Some tetrazole derivatives have been disclosed in the past but none of them has been described as possessing a potassium channel modulating activity.

For example, EP-A-0495626 discloses tetrazole derivatives falling within the following general formula and their use as angiotensins (II) inhibitors:

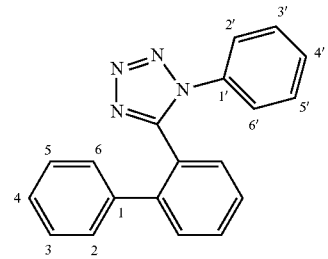

Compounds disclosed in this patent application are substituted in the 4-position but remain unsubstituted in the 2-position.

It has now been surprisingly discovered that new tetrazole derivatives may be used as potassium channel modulating agents and are therefore useful for treating, alleviating or preventing chronic inflammation disorders.

Accordingly, the present invention relates to a new tetrazole derivative of general formula (I):

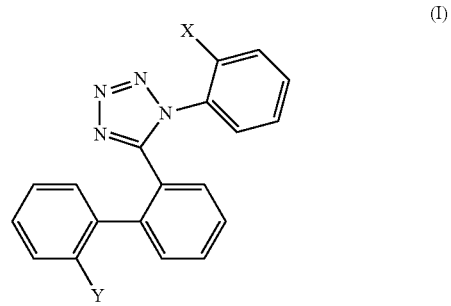

in which:
— X is chosen as being hydrogen, halogen, hydroxy, cyano, $C_1$-$C_6$-alkyl, $C_1$-$C_6$-haloalkyl or a $C_1$-$C_6$-alkoxy; and
— Y is chosen as being hydrogen, halogen, cyano, hydroxy, amino, carbamoyl, formyl, acetyl, $C_1$-$C_6$-alkyl, $C_1$-$C_6$-alkoxy, $C_1$-$C_6$-haloalkyl, $C_1$-$C_6$-haloalkoxy, $C_1$-$C_6$-cyanoalkyl, $C_1$-$C_6$-cyanoalkoxy, $C_1$-$C_6$-hydroxyalkyl, $C_1$-$C_6$-hydroxyalkoxy, $C_1$-$C_6$-thioalkoxy, $C_1$-$C_6$-alkylsulfinyl, $C_1$-$C_6$-alkylsulfonyl, $C_3$-$C_7$-cycloalkyl, $C_3$-$C_7$-cycloalkyl-$C_1$-$C_6$-alkoxy, $C_1$-$C_6$-alkoxy-$C_1$-$C_6$-alkoxy, $C_1$-$C_6$-alkoxy-carbonyl-$C_1$-$C_6$-alkoxy, acetyl-$C_1$-$C_6$-alkoxy, N,N-di-$C_1$-$C_6$-alkylamino, N—(N,N-di-$C_1$-$C_6$-alkylamino)-$C_1$-$C_6$-alkylamino, N—$C_1$-$C_6$-alkyl-carbonyl-amino, N—($C_1$-$C_6$-alkoxy-$C_1$-$C_6$-alkyl)-amino, N,N-di-$C_1$-$C_6$-alkylamino-$C_1$-$C_6$-alkoxy, N—$C_1$-$C_6$-alkylsulfonyl-amino, N,N-di-$C_1$-$C_6$-sulfonyl-amino, amino-carbonyl-$C_1$-$C_6$-alkoxy, hydroxylamine-$C_1$-$C_6$-alkylidene, benzyl or benzamide;

as well as its pharmaceutically acceptable derivatives and/or its possible stereoisomers.

In the context of the present invention:
"halogen" means chlorine, bromine, iodine or fluorine. Preferably halogen means fluorine or chlorine;
"carbonyl" means —C(=O)—;
"pharmaceutically acceptable derivative" of a compound means any "prodrug" or "metabolite" of said compound, as well as a pharmaceutically acceptable salt thereof;

"prodrug" of a compound means any compound whose biotransformation in the body leads to said compound;

"metabolite" of a compound means any intermediate resulting from the transformation of said compound in the body during a metabolic process;

"pharmaceutically acceptable salt" of a compound designates any "onium" salts of N-containing compounds or any salt of addition of said active principle with a mineral or organic acid among which acetic, hydrochloric, cinnamic, citric, formic, hydrobromic, hydrolodic, hydrofluoric, malonic, methanesulphconic, oxalic, picric, maleic, lactic, nicotinic, phenylacetic, phosphoric, succinic and tartric acid, ammonium, diethylamine, piperazine, nicotinamide, urea, sodium, potassium, calcium, magnesium, zinc, lithium, methylamino, dimethylamino, trimethylamino and tris(hydroxymethyl)aminomethane acid; or a cation among which sodium, potassium, calcium, magnesium, zinc, aluminium, lithium, choline, lysinium and ammonium.

a "pharmaceutically effective amount" means an amount of a compound or of a composition which is capable of preventing, alleviating or treating the symptoms of the various pathological conditions herein described;

"stereoisomer" of a compound designates its enantiomers, diastereoisomers and/or cis-trans-isomers;

"$C_1$-$C_6$-alkyl" designates an alkyl group containing from 1 to 6 carbon atoms that can be linear or branched such as methyl, ethyl, prop-1-yl, prop-2-yl, iso-propyl, tert-butyl, but-1-yl, but-2-yl, pent-1-yl, pent-2-yl, pent-3-yl, 2-methylbut-1-yl, 3-methylbut-1-yl), hex-1-yl or 2,3-dimethylbut-1-yl. Preferably, $C_1$-$C_6$-alkyl designates methyl or ethyl;

"$C_1$-$C_6$-alkylidene" designates a divalent functional groups derived from a $C_1$-$C_6$-alkyl by removal of two hydrogen atoms from the same carbon atom, the free valencies being part of a double bond;

"$C_1$-$C_6$-alkoxy" designates a —O—$C_1$-$C_6$-alkyl group such as methoxy, ethoxy, 1-propoxy, 2-propoxy, 1-butoxy, 2-butoxy, 2-methyl-2-propoxy, 1-pentoxy, 3-methyl-1-butoxy, 2-pentoxy, 2-methyl-2-butoxy, 1-hexoxy or 3-hexoxy. Preferably, $C_1$-$C_6$-alkoxy designates methoxy or ethoxy;

"$C_1$-$C_6$-thioalkoxy" designates a $C_1$-$C_6$-alkoxy in which the oxygen atom has been replaced by a sulphur atom;

"$C_1$-$C_6$-haloalkyl" designates a $C_1$-$C_6$-alkyl substituted by one or further halogen atoms. Preferably, $C_1$-$C_6$-haloalkyl designates halomethyl, more preferably fluoromethyl;

"$C_1$-$C_6$-haloalkyl" or "$C_1$-$C_6$-haloalkoxy" designates respectively a $C_1$-$C_6$-alkyl or a $C_1$-$C_6$-alkoxy substituted by one or further halogen atoms. Preferably, $C_1$-$C_6$-haloalkoxy designates halomethoxy or dihalomethoxy, more preferably fluoromethoxy, chloromethoxy, difluoromethoxy or dichloromethoxy;

"$C_1$-$C_6$-cyanoalkyl" or "$C_1$-$C_6$-cyanoalkoxy" designates respectively a $C_1$-$C_6$-alkyl or a $C_1$-$C_6$-alkoxy substituted by one or further cyano groups;

"$C_1$-$C_6$-hydroxyalkyl" or "$C_1$-$C_6$-hydroxyalkoxy" designates respectively a $C_1$-$C_6$-alkyl or a $C_1$-$C_6$-alkoxy substituted by one or further hydroxy groups;

"$C_3$-$C_7$-cycloalkyl" designates a saturated monocyclic carbocyclic ring containing from 3 to 7 carbon atoms such as cyclopropyl, cyclobutyl, cyclopentyl, cyclohexyl or cycloheptyl.

Compounds of the present invention are active as potassium channel modulators. They are therefore of great interest for the treatment, alleviation and/or prevention of chronic inflammation disorders.

The present invention relates to a compound of general formula (I). Preferably compound of general formula (I) according to the present invention have the following characteristics, taken individually or in combination:

X is chosen as being hydrogen, halogen, hydroxy, cyano, $C_1$-$C_6$-alkoxy or $C_1$-$C_6$-haloalkoxy. More preferably, X is chosen as being hydrogen, fluorine, chlorine, hydroxy, cyano, methoxy, fluoromethoxy, chloromethoxy, difluoromethoxy or dichloromethoxy; and/or Y is chosen as being hydrogen, halogen, cyano, hydroxy, amino, carbamoyl, formyl, acetyl, $C_1$-$C_6$-alkyl, $C_1$-$C_6$-alkoxy, $C_1$-$C_6$-halo alkyl, $C_1$-$C_6$-halo alkoxy, $C_1$-$C_6$-cyano alkoxy, $C_1$-$C_6$-hydroxyalkyl, $C_1$-$C_6$-thioalkoxy, $C_1$-$C_6$-alkylsulfinyl, $C_1$-$C_6$-alkylsulfonyl, $C_3$-$C_7$-cyclo alkyl-$C_1$-$C_6$-alkoxy, $C_1$-$C_6$-alkoxy-$C_1$-$C_6$-alkoxy, $C_1$-$C_6$-alkoxy-carbonyl-$C_1$-$C_6$-alkoxy, acetyl-$C_1$-$C_6$-alkoxy, N,N-di-$C_1$-$C_6$-alkylamino, N—(N,N-di-$C_1$-$C_6$-alkylamino)-$C_1$-$C_6$-alkylamino, N—$C_1$-$C_6$-alkyl-carbonyl-amino, N—($C_1$-$C_6$-alkoxy-$C_1$-$C_6$-alkyl)-amino, N,N-di-$C_1$-$C_6$-alkylamino-$C_1$-$C_6$-alkoxy, N—$C_1$-$C_6$-alkylsulfonyl-amino, N,N-di-$C_1$-$C_6$-sulfonyl-amino, amino-carbonyl-$C_1$-$C_6$-alkoxy, hydroxylamine-$C_1$-$C_6$-alkylidene, benzyl or benzamide. More preferably, Y is chosen as being halogen, cyano, amino, formyl, $C_1$-$C_6$-alkyl, $C_1$-$C_6$-alkoxy, $C_1$-$C_6$-halo alkyl, $C_1$-$C_6$-halo alkoxy, $C_1$-$C_6$-cyano alkoxy, $C_1$-$C_6$-hydroxyalkyl, $C_1$-$C_6$-thioalkoxy, $C_3$-$C_7$-cycloalkyl-$C_1$-$C_6$-alkoxy, $C_1$-$C_6$-alkoxy-$C_1$-$C_6$-alkoxy, $C_1$-$C_6$-alkoxy-carbonyl-$C_1$-$C_6$-alko xy, N,N-di-$C_1$-$C_6$-alkylamino, N—($C_1$-$C_6$-alkoxy-$C_1$-$C_6$-alkyl)-amino, amino-carbonyl-$C_1$-$C_6$-alkoxy or hydroxylamine-$C_1$-$C_6$-alkylidene. Even more preferably, Y is chosen as being fluorine, chlorine, cyano, amino, formyl, ethyl, methoxy, ethoxy, fluoromethoxy, difluoromethoxy, halomethoxy, cyanomethoxy, thiomethoxy, methoxy-ethoxy, hydroxylamine-methylidene or benzamide.

More preferably, the present invention relates to a compound of general formula (I) as defined above in which X is chosen as being hydrogen, fluorine, chlorine, hydroxy, cyano, methoxy, fluoromethoxy, chloromethoxy, difluoromethoxy or dichloromethoxy; and Y is chosen as being halogen, cyano, amino, formyl, ethyl, methoxy, ethoxy, fluoromethoxy, difluoromethoxy, halomethoxy, cyanomethoxy, thiomethoxy, methoxy-ethoxy, hydroxylamine-methylidene or benzamide.

Suitable examples of compounds according to the present invention include the following tetrazole derivatives:

2-{2-[1-(2-Fluorophenyl)-1H-1,2,3,4-tetrazol-5-yl] phenyl}phenol;

5-[2-(2-Ethoxyphenyl)phenyl]-1-(2-fluorophenyl)-1H-1,2,3,4-tetrazole;

1-(2-Fluorophenyl)-5-{2-[2-(2-methoxyethoxyl)phenyl] phenyl}-1H-1,2,3,4-tetrazole;

5-{2-[2-(Difluoromethoxy)phenyl]phenyl}-1-(2-fluorophenyl)-1H-1,2,3,4-tetrazole;

1-(2-Fluorophenyl)-5-(2-phenylphenyl)-1H-1,2,3,4-tetrazole;

5-{2-[2-(Cyclopropylmethoxy)phenyl]phenyl}-1-(2-fluorophenyl)-1H-1,2,3,4-tetrazole;

2-(2-{2-[1-(2-Fluorophenyl)-1H-1,2,3,4-tetrazol-5-yl] phenyl}phenoxy)acetonitrile;

methyl 2-(2-{2-[1-(2-fluorophenyl)-1H-1,2,3,4-tetrazol-5-yl]phenyl}phenoxy)acetate;
1-(2-Fluorophenyl)-5-{2-[2-(propan-2-yloxy)phenyl]phenyl}-1H-1,2,3,4-tetrazole;
5-{2-[2-(Fluoromethoxy)phenyl]phenyl}-1-(2-fluorophenyl)-1H-1,2,3,4-tetrazole;
1-(2-Fluorophenyl)-5-[2-(2-methoxyphenyl)phenyl]-1H-1,2,3,4-tetrazole;
1-(2-Fluorophenyl)-5-{2-[2-(methylthio)phenyl]phenyl}-1H-1,2,3,4-tetrazole;
1-(2-Fluorophenyl)-5-{2-[2-(trifluoromethoxy)phenyl]phenyl}-1H-1,2,3,4-tetrazole;
1-(2-Fluorophenyl)-5-{2-[2-(methoxymethoxy)phenyl]phenyl}-1H-1,2,3,4-tetrazole;
2-(2-{2-[1-(2-Fluorophenyl)-1H-1,2,3,4-tetrazol-5-yl]phenyl}phenoxy)acetamide;
1-(2-Fluorophenyl)-5-[2-(2-methylphenyl)phenyl]-1H-1,2,3,4-tetrazole;
5-[2-(2-Ethylphenyl)phenyl]-1-(2-fluorophenyl)-1H-1,2,3,4-tetrazole;
2-{2-[1-(2-Fluorophenyl)-1H-1,2,3,4-tetrazol-5-yl]phenyl}benzaldehyde;
1-(2-Fluorophenyl)-5-{2-[2-(trifluoromethyl)phenyl]phenyl}-1H-1,2,3,4-tetrazole;
5-[2-(2-Bromophenyl)phenyl]-1-(2-fluorophenyl)-1H-1,2,3,4-tetrazole;
5-[2-(2-Chlorophenyl)phenyl]-1-(2-fluorophenyl)-1H-1,2,3,4-tetrazole;
1-(2-Fluorophenyl)-5-[2-(2-fluorophenyl)phenyl]-1H-1,2,3,4-tetrazole;
2-{2-[1-(2-Fluorophenyl)-1H-1,2,3,4-tetrazol-5-yl]phenyl}-N,N-dimethylaniline;
2-{2-[1-(2-Fluorophenyl)-1H-1,2,3,4-tetrazol-5-yl]phenyl}aniline;
1-(2-Fluorophenyl)-5-{2-[2-(methoxymethyl)phenyl]phenyl}-1H-1,2,3,4-tetrazole;
(2-{2-[1-(2-Fluorophenyl)-1H-1,2,3,4-tetrazol-5-yl]phenyl}phenyl)methanol;
(E)-N-[(2-{2-[1-(2-Fluorophenyl)-1H-1,2,3,4-tetrazol-5-yl]phenyl}phenyl)methylidene]hydroxylamine;
2-{2-[1-(2-Fluorophenyl)-1H-1,2,3,4-tetrazol-5-yl]phenyl}benzonitrile;
5-{2-[2-(Difluoromethyl)phenyl]phenyl}-1-(2-fluorophenyl)-1H-1,2,3,4-tetrazole;
5-{2-[2-(Fluoromethyl)phenyl]phenyl}-1-(2-fluorophenyl)-1H-1,2,3,4-tetrazole;
2-{2-[1-(2-Fluorophenyl)-1H-1,2,3,4-tetrazol-5-yl]phenyl}-N-(2-methoxyethyl)aniline;
1-(2-Chlorophenyl)-5-[2-(2-fluorophenyl)phenyl]-1H-1,2,3,4-tetrazole;
1-(2-Chlorophenyl)-5-[2-(2-methoxyphenyl)phenyl]-1H-1,2,3,4-tetrazole;
1-(2-Methoxyphenyl)-5-[2-(2-methoxyphenyl)phenyl]-1H-1,2,3,4-tetrazole;
2-{5-[2-(2-Methoxyphenyl)phenyl]-1H-1,2,3,4-tetrazol-1-yl}phenol;
5-[2-(2-Fluorophenyl)phenyl]-1-(2-methoxyphenyl)-1H-1,2,3,4-tetrazole;
2-{5-[2-(2-Methoxyphenyl)phenyl]-1H-1,2,3,4-tetrazol-1-yl}benzonitrile;
1-[2-(Difluoromethoxy)phenyl]-5-[2-(2-fluorophenyl)phenyl]-1H-1,2,3,4-tetrazole;
1-[2-(Difluoromethoxy)phenyl]-5-[2-(2-methoxyphenyl)phenyl]-1H-1,2,3,4-tetrazole;
2-(5-{2-[2-(Difluoromethoxy)phenyl]phenyl}-1H-1,2,3,4-tetrazol-1-yl)benzonitrile; and
1-phenyl-5-(2-phenylphenyl)-1H-1,2,3,4-tetrazole.

Compounds according to the present invention may be prepared according to any conventional methods of chemical synthesis known by the skilled artisan. The starting materials for the processes described in the present application are known or may readily be prepared by conventional methods known by the skilled artisan from commercially available chemicals.

The end products of the reactions described herein may be isolated by conventional technique such as extraction, crystallisation, distillation or chromatography.

The present invention also relates to a pharmaceutical composition comprising, as an active ingredient, a pharmaceutically effective amount of a compound of general formula (I) as defined above. Preferably, the pharmaceutical composition according to the present invention contain from 0.5 to 2000 mg of a compound of formula (I) as defined above.

The present invention also relates to a pharmaceutical composition comprising a pharmaceutically effective amount of a compound general formula (I) associated to one or further known immune-suppressants or with 5-amino salicylic acid for the treatment or alleviation of a diseases, disorders or condition related to immune dysfunction, or for obtaining immune suppression. Examples of immune-suppressants to combine with the compounds of Formula (I) include amphotericin, budesonide, busulphan, co-trimoxazole, chlorambucil, colony stimulating factors, corticosteroids, cyclophosphamide, fluconazole, folinic acid, ganciclovir, antilymphocyte immunoglobulins, normal immunoglobulins, methotrexate, methylprednisolone, octreotide, oxpentifylline, tacrolimus (FK506), thalidomide, zolimomab aritox, and the calcineurin inhibitors (protein phosphatase 2B inhibitors), in particular cyclosporin.

The pharmaceutical compositions according to the present invention may be formulated under any form generally used in the pharmaceutical field. As an example, these may involve pharmaceutical vectors such as salts or electrolytes, salts of ascorbic acid, water or buffered solutions, colloidal solutions, substances based on cellulose, polyethylene glycol, polyacrylates, waxes, proteins or any other substance capable of dissolving or rendering the active compound available for therapeutic action.

The compositions of the present invention may be administered in injectable form or via the oral or parenteral route, via the nasal route in spray form, via the rectal or vaginal route, by implantation of a reservoir or dispensers or in any other pharmaceutical form used in the pharmaceutical field.

The injectable forms of these compositions may be aqueous or oily suspensions. These suspensions may be formulated according to any process used in this field by using non-toxic solvents or diluents such as 1,3-butanediol for example. Among the acceptable solvents, it is possible to use water, buffered solutions, Ringer solutions, or isotonic salt solutions. Other acceptable diluents may be formed of synthetic mono or di-glycerides, long-chain alcohols, or dispersants such as carboxymethyl cellulose or any other diluent or emulsifier used in formation of pharmaceutical suspensions. The pharmaceutical compositions of the present invention administered via the oral route may be in the form of capsules, tablets or aqueous suspensions or in the form of emulsions. These formulations may possibly contain chemical compounds intended to attenuate or improve the taste.

The pharmaceutical compositions of the present invention may be administered in suppository form by mixing the product with a non-irritant, non-allergic, excipient, solid at ambient temperature and liquid at rectal temperature in order to release the active compound. Such formulations may for example use beeswax, polyethylene glycols or cocoa butter.

The pharmaceutical composition according to the present invention is useful for treating, alleviating and/or preventing chronic inflammation disorders. Said composition indeed allows modulating potassium channel. Accordingly, the present invention also relates to a pharmaceutical composition as defined above for its use for the treatment, alleviation and/or prevention of chronic inflammation disorders. Examples of chronic inflammation disorders include inflammatory bowel disease (IBD) among which ulcerative colitis (UC) and Crohn's disease (CD), rheumatoid arthritis (RA), multiple sclerosis (MS) and asthma.

The present invention further relates to the use of a compound of formula (I) as defined above for the preparation of a medicament for treatment, alleviation and/or prevention of chronic inflammation disorders. The present invention also relates to the use of a compound of formula (I) as defined above for the preparation of a medicament for the treatment, alleviation and/or prevention of inflammatory bowel disease (IBD) among which ulcerative colitis (UC) and Crohn's disease (CD), rheumatoid arthritis (RA), multiple sclerosis (MS) and asthma.

Finally, the present invention further relates to a method of treatment, alleviation and/or prevention of chronic inflammation disorders by administering to an individual a compound of formula (I) as defined above. The present invention also relates to a method a method of treatment, alleviation and/or prevention of inflammatory bowel disease (IBD) among which ulcerative colitis (UC) and Crohn's disease (CD), rheumatoid arthritis (RA), multiple sclerosis (MS) and asthma, by administering to an individual a compound of formula (I) as defined above.

The present invention will now be illustrated in a non-limited manner with reference to the following examples.

EXAMPLE 1

Processes for Preparing Compounds According to the Present Invention

Example 1.1

Process for Preparing 1-(2-fluorophenyl)-5-(2-iodo-phenyl)-1H-1,2,3,4-tetrazole (Compound 1)

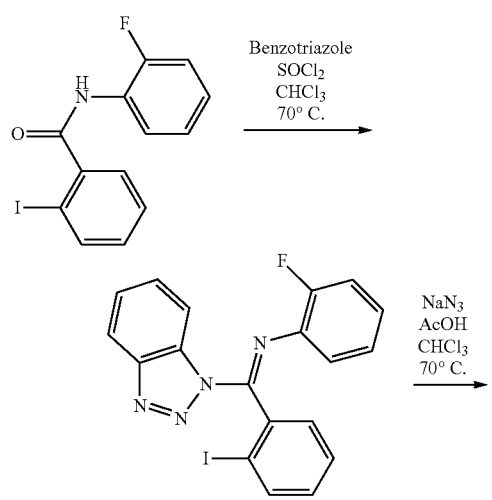

-continued

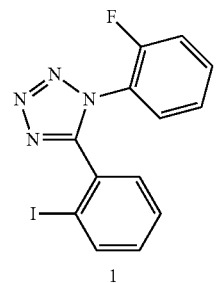

1

To a solution of N-(2-fluorophenyl)-2-iodobenzamide (10 g) in chloroform (80 ml) were added thionyl chloride (5.4 ml) and benzotriazole (14.1 g) and the reaction mixture was heated in a pressure tube at 70° C. After 20 hours the reaction mixture was quenched with ice-water and extracted with ethyl acetate (250 ml*3). The organic layer was washed with 10% sodium bicarbonate solution (75 ml*3), water (100 ml) and brine (100 ml), dried over anhydrous sodium sulphate, filtered and concentrated under reduced pressure to afford the benzotriazolyl intermediate (14 g) as brown gum.

To a solution of 10 g of this material in chloroform (100 ml) was added sodium azide (5.9 g) followed by acetic acid (2.6 ml) resulting in a cloudy white precipitate. The reaction mixture was heated at 60° C. After 48 hours the reaction mixture was cooled to room temperature and concentrated under reduced pressure to remove acetic acid. The residue was diluted with chloroform (350 ml), washed with 10% sodium bicarbonate solution (50 ml*3) and brine (50 ml*3).

The organic phase was then dried over anhydrous sodium sulphate, filtered and concentrated under reduced pressure to afford 10.2 g of a yellow gum which was purified by column chromatography over silica gel (230-400 mesh, eluent: CHCl$_3$) to afford the desired 1-(2-fluorophenyl)-5-(2-iodo-phenyl)-1H-1,2,3,4-tetrazole (1) as an off-white solid (7.8 g, 90%).

Example 1.2

Process for Preparing 2-{2-[1-(2-Fluorophenyl)-1H-1,2,3,4-tetrazol-5-yl]phenyl}phenol (Compound 2)

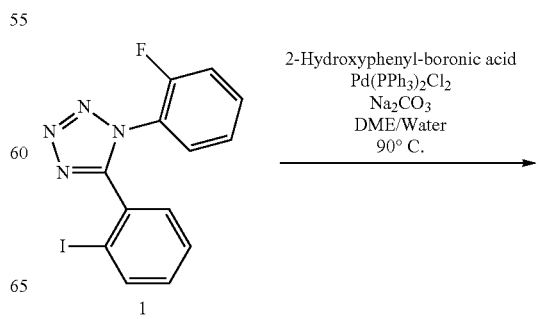

1

-continued

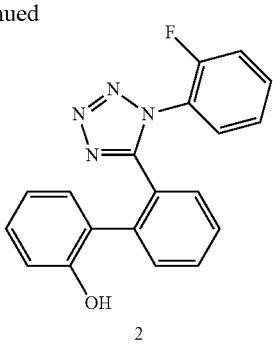

2

To a solution of 1 (1 g) and 2-hydroxylphenylboronic acid (753 mg) in a mixture of 1,2 dimethoxyethane (12 ml) and water (4 ml) was added sodium carbonate (724 mg). The reaction mixture was purged with nitrogen for 5 min. and then bis(triphenylphosphine)palladium (II) dichloride (96 mg) was added. The reaction mixture was heated at 90° C. for 3 hrs and at room temperature for 41 hours. The reaction mixture concentrated under reduced pressure and the residue was diluted with water (10 ml) and extracted with chloroform (50 ml*3). The combined organic layers were washed with brine (50 ml), dried over anhydrous sodium sulfate, filtered and concentrated to afford the coupled phenol as a black gum (1.1 g) which was purified by column chromatography over silica gel (230-400 mesh, eluent: 3% MeOH in chloroform) to provide 2 an off-white solid (580 mg, 64%, MP=209.9-211.2° C.; MH$^+$ (found)=333.11466, MH$^+$(calc)=333.114619).

Example 1.3

Process for Preparing 5-[2-(2-Ethoxyphenyl)phenyl]-1-(2-fluorophenyl)-1H-1,2,3,4-tetrazole (Compound 3)

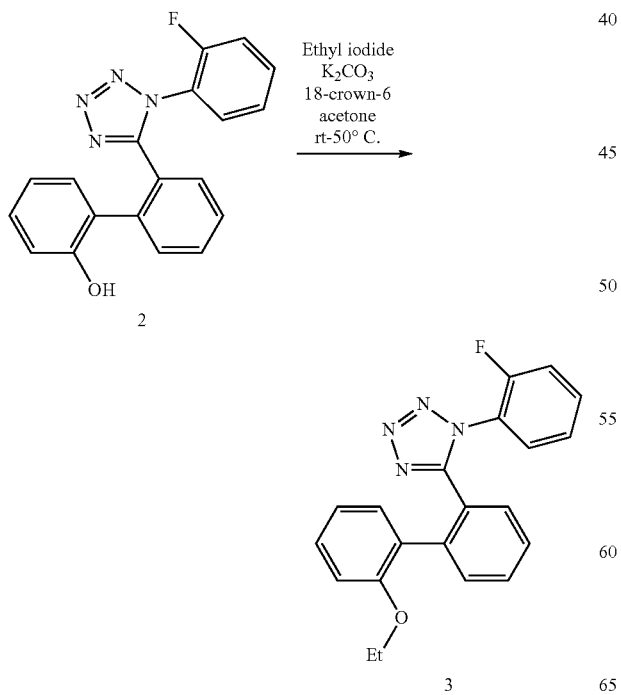

To a solution of 2 (300 mg) in acetone (10 ml) were added potassium carbonate (312 mg) and 18-crown-6 (24 mg). The mixture was cooled to 0° C. and a solution of iodoethane (0.14 ml) in acetone (5 ml) was added. After completion of addition the reaction mixture was stirred with slow warming to rt. After 14 hours the reaction mixture was again cooled to 0° C. and a solution of iodoethane (0.07 ml) in acetone (5 ml) was added. After completion of addition the reaction mixture was stirred with slow warming to rt.

Then reaction mixture was heated at 50° C. After 24 hours the reaction mixture was concentrated under reduced pressure to remove acetone, the residue was diluted with water (15 ml) and extracted with ethyl acetate (3*50 ml).

The combined organic layer was washed with brine (20 ml), dried over anhydrous sodium sulfate, filtered and concentrated under reduced pressure to afford a colourless gum (290 mg) which was purified by column chromatography over silica gel (230-400 mesh, eluent: 8% ethyl acetate in hexane) to afford the ethyl ether 3 as an off-white solid (135 mg, 42%, MP=133.2-134.8° C.; MH$^+$(found)=361.14645, MH$^+$(calc)=361.145919).

Example 1.4

Process for Preparing 1-(2-Fluorophenyl)-5-{2-[2-(2-methoxyethoxy)phenyl]phenyl}-1H-1,2,3,4-tetrazole (Compound 4)

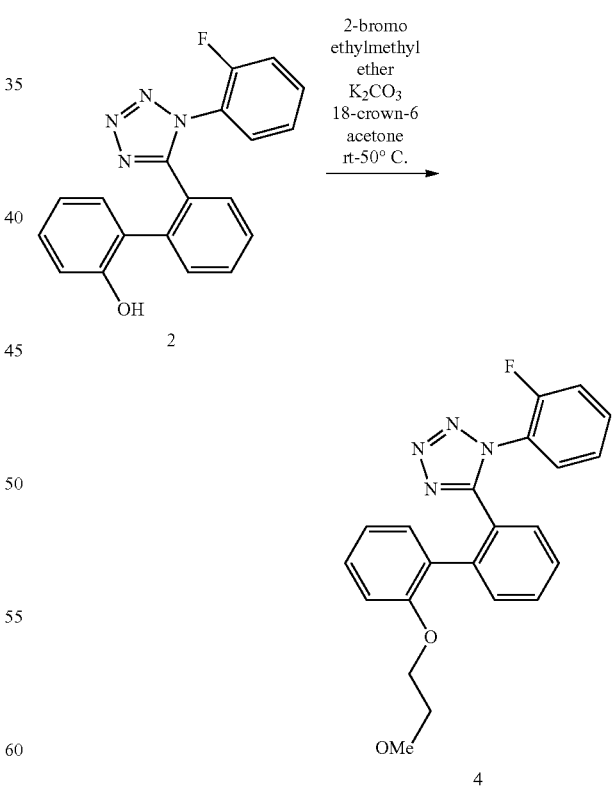

Compound 4 was prepared in 67% yield as a white solid (MP=76.6-78.1° C.; MH$^+$(found)=391.15657, MH$^+$(calc)=391.156484) from 2 in a similar fashion to Compound 3, using 2-bromo ethylmethyl ether.

Example 1.5

Process for Preparing 5-{2-[2-(Difluoromethoxy)phenyl]phenyl}-1-(2-fluorophenyl)-1H-1,2,3,4-tetrazole (Compound 5) and 1-(2-Fluorophenyl)-5-(2-phenylphenyl)-1H-1,2,3,4-tetrazole (Compound 40)

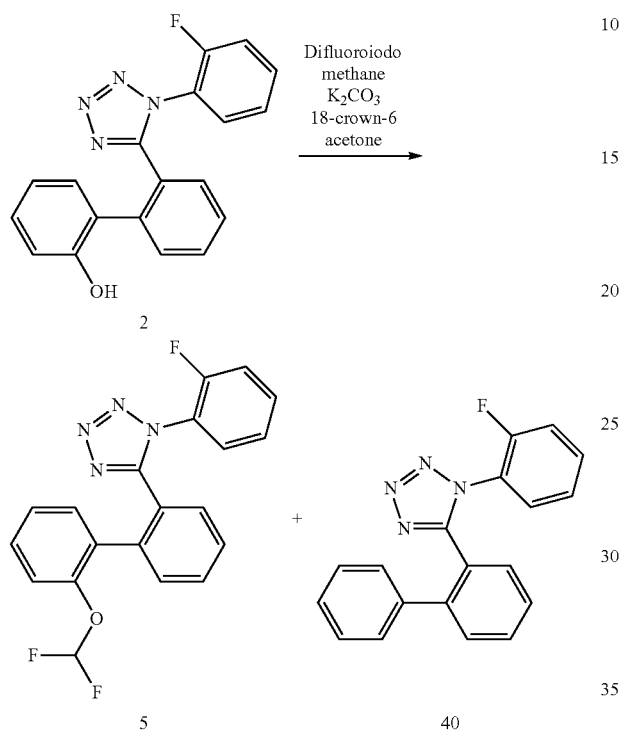

Compound 5 was prepared in 69% yield as an off-white solid (MP=88-90° C.; MH+(found)=383.11189, MH+(calc)=383.111425) from 2 in a similar fashion to Compound 3, using difluoroiodomethane. Compound 40 was isolated as a very small amount of side product (1%) in a large scale preparation of 5 using 2 and freon in propanol containing 5% aq. sodium hydroxide.

Example 1.6

Process for Preparing 5-{2-[2-(Cyclopropylmethoxy)phenyl]phenyl}-1-(2-fluorophenyl)-1H-1,2,3,4-tetrazole (Compound 6)

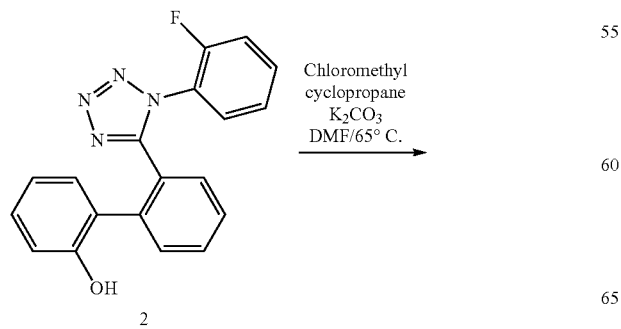

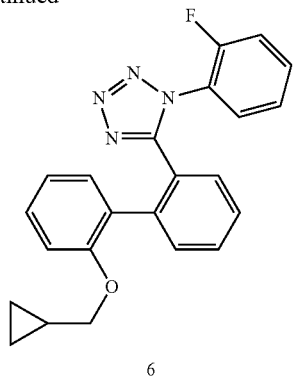

Compound 6 was prepared in 57% yield as a light yellow solid (MP=120.3-121.7° C.; MH+(found)=387.16241, MH+(calc)=387.161569) from 2 in a similar fashion to Compound 3, using chloromethylcyclopropane.

Example 1.7

Process for Preparing 2-(2-{2-[1-(2-Fluorophenyl)-1H-1,2,3,4-tetrazol-5-yl]phenyl}phenoxy)acetonitrile (Compound 7)

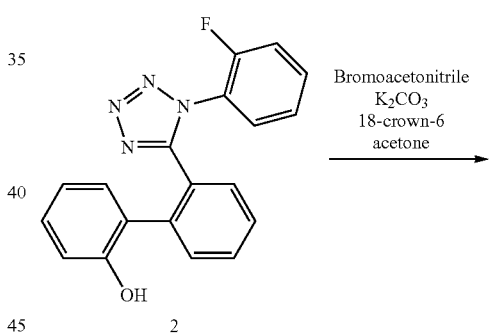

Compound 7 was prepared in 77% yield as an off-white solid (MP=125.2-127.1° C.; MH+(found)=372.12597, MH+(calc)=372.125518) from 2 in a similar fashion to Compound 3, using bromoacetonitrile.

Example 1.8

Process for Preparing Methyl 2-(2-{2-[1-(2-fluorophenyl)-1H-1,2,3,4-tetrazol-5-yl]phenyl}phenoxy)acetate (Compound 8)

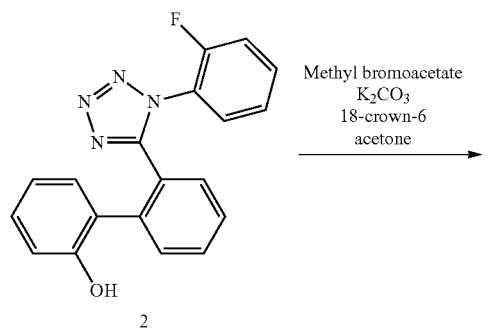

Compound 8 was prepared in 79% yield as a white solid (MP=165.1-166.8° C.; MH+(found)=405.13449, MH+(calc)=405.135749) from 2 in a similar fashion to Compound 3, using methyl bromoacetate.

Example 1.9

Process for Preparing 1-(2-Fluorophenyl)-5-{2-[2-(propan-2-yloxy)phenyl]phenyl}-1H-1,2,3,4-tetrazole (Compound 9)

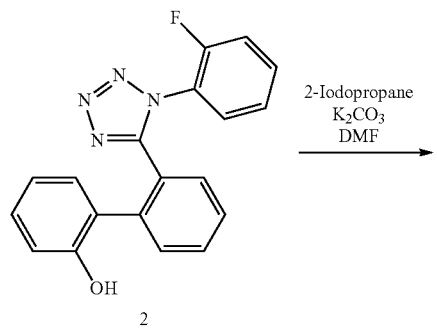

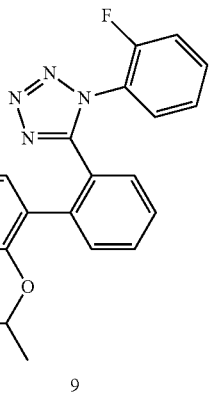

Compound 9 was prepared in 75% yield as a brown solid (MP=128.4-129.6° C.; MH+(found)=375.16299, MH+(calc)=375.161569) from 2 in a similar fashion to Compound 3, using 2-iodopropane.

Example 1.10

Process for Preparing 5-{2-[2-(Fluoromethoxy)phenyl]phenyl}-1-(2-fluorophenyl)-1H-1,2,3,4-tetrazole (Compound 12)

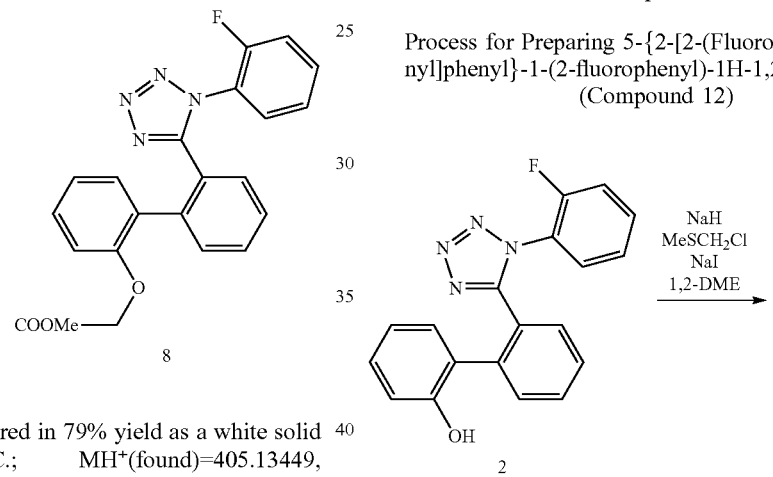

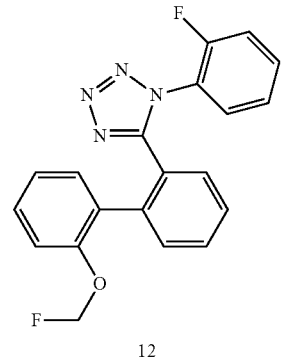

To a suspension of sodium hydride (181 mg) in 1,2-dimethoxyethane (25 ml) was added Compound (2) (1 g) at 0° C. and the reaction mixture was stirred at 0° C. After 15 minutes chloromethyl methyl sulfide (0.38 ml) followed by sodium iodide (45 mg) were added at 0° C. The reaction mixture was stirred with slow warming to rt. After 14 hours, the reaction mixture was quenched with ice-water (75 ml). The product was then extracted with dichloromethane (100 ml*3). The combined organic layer was washed with water (50 ml), brine (50 ml), dried over anhydrous sodium sulphate, filtered and concentrated under reduced pressure to afford the corresponding crude (methylthio)methyl ether as a brown gum (1.32 g). To 1 gram of this crude product in dichloromethane (25 ml) was added sulfuryl chloride (0.32 ml) at 0° C. After the completion of addition the reaction mixture was stirred with slow warming to rt. After 1.5 hours, the reaction mixture was quenched with ice-water (75 ml). The product was then extracted with dichloromethane (100 ml*3). The combined organic layer was dried over anhydrous sodium sulphate, filtered and concentrated under reduced pressure to afford the crude intermediate chloromethyl ether as a brown gum (1.2 g) which was dissolved in dichloromethane (25 ml) and treated with a 1M solution of tetrabutylammoniumfluoride in THF (2.3 ml) at 0° C. After the completion of the addition, the reaction mixture was stirred with slow warming to rt. After 2.5 hours, the reaction mixture was quenched with ice-water (75 ml). The crude product was then extracted with dichloromethane (100 ml*3). The combined organic layer was washed with brine (75 ml), dried over anhydrous sodium sulphate, filtered and concentrated under reduced pressure to afford a brown gum (1.4 g) which was purified by flash column chromatography over silica gel (230-400 mesh, eluent: 8% ethylacetate in hexane) to afford a yellowish gum (460 mg) which was dissolved in a mixture of diethyl ether:hexane (1:1, 2 ml). The off-white solid formed was filtered, washed with hexane and dried under vacuum to yield the desired fluoromethyl ether (12) (412 mg, 43%, yield). (MP=88.8-90.1° C.; MH$^+$(found)=365.12112, MH$^+$(calc)=365.120847).

Example 1.11

Process for Preparing 1-(2-Fluorophenyl)-5-[2-(2-methoxyphenyl)phenyl]-1H-1,2,3,4-tetrazole (Compound 13)

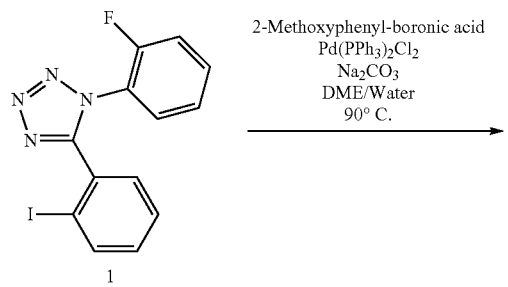

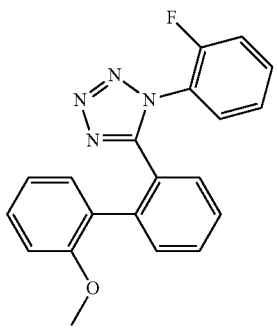

13

Compound 13 was prepared in 52% yield as a white solid (MP=123.3-124.8° C.; MH$^+$(found)=347.12944, MH$^+$(calc)=347.130269) from 1 in a similar fashion to Compound 2 using 2-methoxyphenyl-boronic acid.

Example 1.12

Process for Preparing 1-(2-Fluorophenyl)-5-{2-[2-(methylthio)phenyl]phenyl}-1H-1,2,3,4-tetrazole (Compound 14)

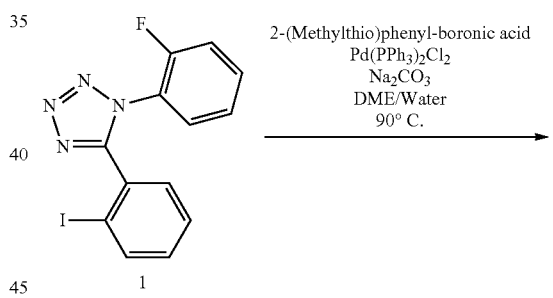

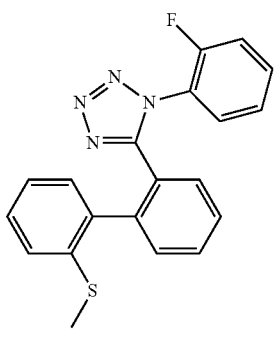

14

Compound 14 was prepared in 62% yield as a white solid (MP=127.2-129.1° C.; MH$^+$(found)=363.10696, MH$^+$(calc)=363.107425) from 1 in a similar fashion to Compound 2 using 2-(methylthio)phenyl-boronic acid.

Example 1.13

Process for Preparing 1-(2-Fluorophenyl)-5-{2-[2-(trifluoromethoxy)phenyl]phenyl}-1H-1,2,3,4-tetrazole (Compound 15)

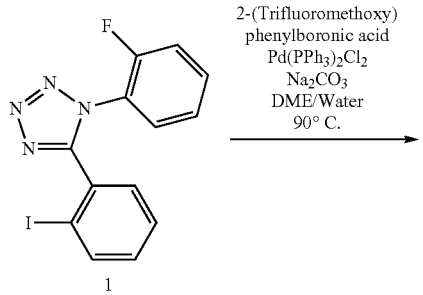

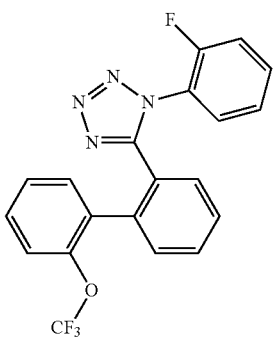

Compound 15 was prepared in 37% yield as an off-white solid (MP=107.2-108.8° C.; MH⁺(found)=401.10176, MH⁺(calc)=401.102003) from 1 in a similar fashion to Compound 2 using 2-(trifluoromethoxy)phenyl-boronic acid.

Example 1.14

Process for Preparing 1-(2-Fluorophenyl)-5-{2-[2-(methoxymethoxy)phenyl]phenyl}-1H-1,2,3,4-tetrazole (Compound 16)

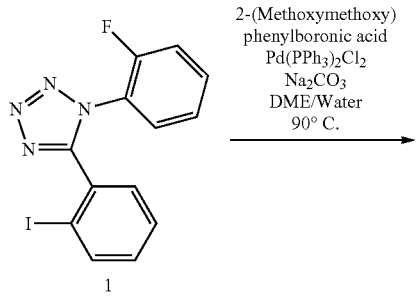

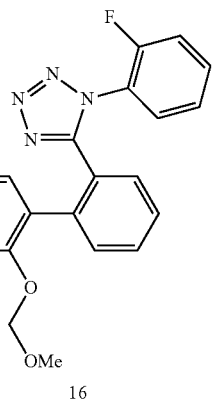

Compound 16 was prepared in 82% yield as an off-white solid (MP=120.1-121.2° C.; MH⁺(found)=399.12361, MH⁺(calc)=399.122804) from 1 in a similar fashion to Compound 2 using 2-(methoxymethoxy)phenylboronic acid.

Example 1.15

Process for Preparing 2-(2-{2-[1-(2-Fluorophenyl)-1H-1,2,3,4-tetrazol-5-yl]phenyl}phenoxy)acetamide (Compound 17)

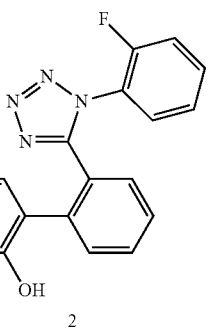

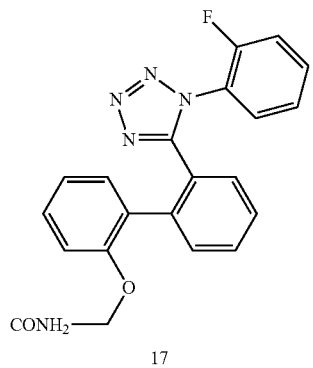

Compound 17 was prepared in 37% yield as an off-white solid (MP=174.4-176.2° C.; MH⁺(found)=390.13646, MH⁺(calc)=390.136083) from 2 in a similar fashion to Compound 3, using 2-bromoacetamide.

Example 1.16

Process for Preparing 1-(2-Fluorophenyl)-5-[2-(2-methylphenyl)phenyl]-1H-1,2,3,4-tetrazole (Compound 19)

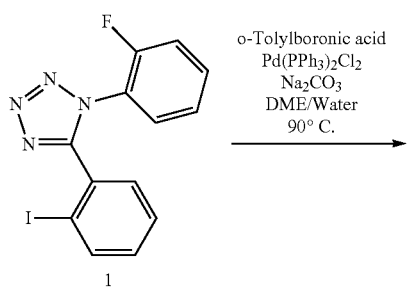

Compound 19 was prepared in 35% yield as an off-white solid (MP=129.5-130.9° C.; MH+(found)=331.13559, MH+ (calc)=331.135354) from 1 in a similar fashion to Compound 2 using o-tolylboronic acid.

Example 1.17

Process for Preparing 5-[2-(2-Ethylphenyl)phenyl]-1-(2-fluorophenyl)-1H-1,2,3,4-tetrazole (Compound 20)

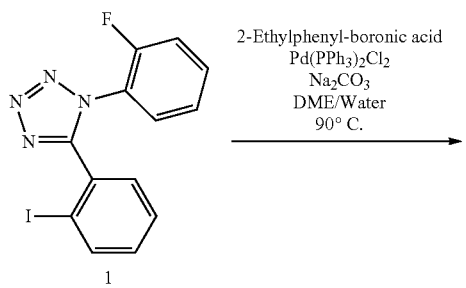

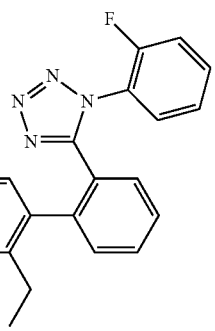

Compound 20 was prepared in 30% yield as an off-white solid (MP=118.2-119.6° C.; MH+(found)=345.15129, MH+ (calc)=345.151004) from 1 in a similar fashion to Compound 2 using 2-ethylphenylboronic acid.

Example 1.18

Process for Preparing 2-{2-[1-(2-Fluorophenyl)-1H-1,2,3,4-tetrazol-5-yl]phenyl}benzaldehyde (Compound 21)

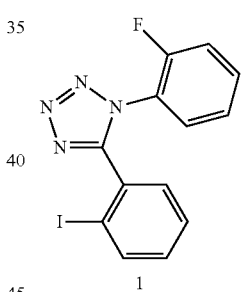
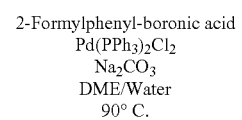

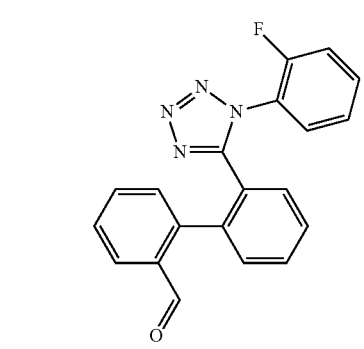

Compound 21 was prepared in 74% yield as an off-white solid (MP=148.2-149.2° C.; MH+(found)=345.11457, MH+ (calc)=345.114619) from 1 in a similar fashion to Compound 2 using 2-ethylphenylboronic acid.

Example 1.19

Process for Preparing 1-(2-Fluorophenyl)-5-{2-[2-(trifluoromethyl)phenyl]phenyl}-1H-1,2,3,4-tetrazole (Compound 22)

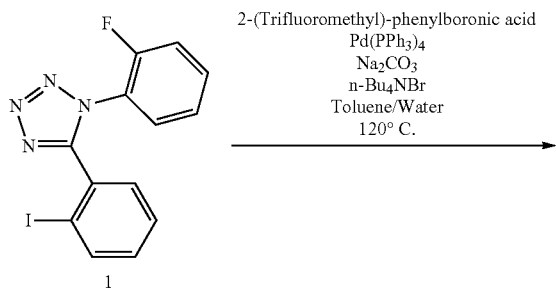

Compound 22 was prepared in 9% yield as an off-white solid (MP=97.3-99.8° C.; MH+(found)=385.10701, MH+ (calc)=385.107088) from 1 in a similar fashion to Compound 2 using 2-(trifluromethyl)phenylboronic acid.

Example 1.20

Process for Preparing 5-[2-(2-Bromophenyl)phenyl]-1-(2-fluorophenyl)-1H-1,2,3,4-tetrazole (Compound 23)

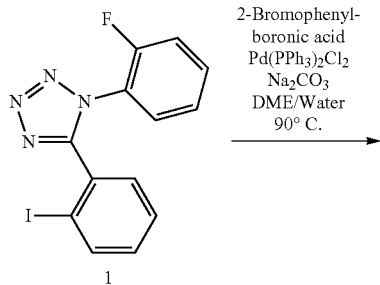

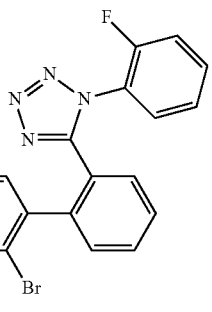

Compound 23 was prepared in 66% yield as an off-white solid (MP=81.6-83.5° C.; MH+(found)=395.02985, MH+ (calc)=395.030217) from 1 in a similar fashion to Compound 2 using 2-bromophenylboronic acid.

Example 1.21

Process for Preparing 5-[2-(2-Chlorophenyl)phenyl]-1-(2-fluorophenyl)-1H-1,2,3,4-tetrazole (Compound 24)

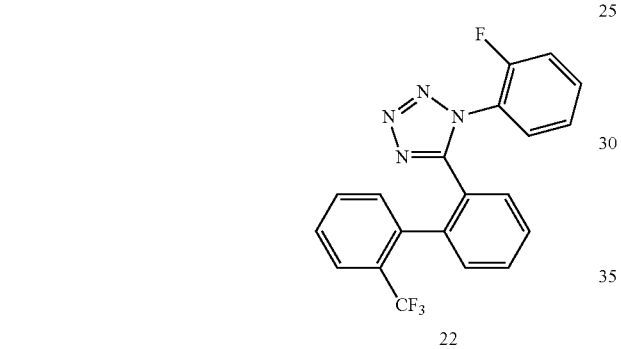

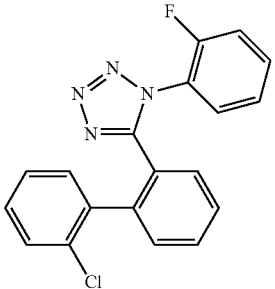

Compound 24 was prepared in 36% yield as a white solid (MP=102.5-103.7° C.; MH+(found)=351.08082, MH+ (calc)=351.080732) from 1 in a similar fashion to Compound 2 using 2-chlorophenylboronic acid.

Example 1.22

Process for Preparing 1-(2-Fluorophenyl)-5-[2-(2-fluorophenyl)phenyl]-1H-1,2,3,4-tetrazole (Compound 25)

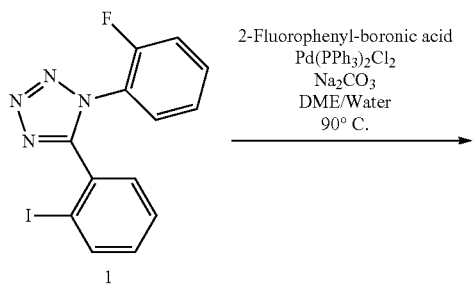

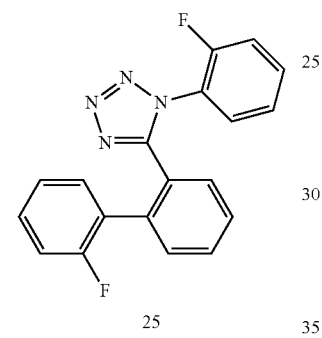

Compound 25 was prepared in 60% yield as a white solid (MP=139.6-141.9° C.; MH$^+$(found)=335.10986, MH$^+$(calc)=335.110282) from 1 in a similar fashion to Compound 2 using 2-fluorophenylboronic acid.

Example 1.23

Process for Preparing 2-{2-[1-(2-Fluorophenyl)-1H-1,2,3,4-tetrazol-5-yl]phenyl}-N,N-dimethylaniline (Compound 26)

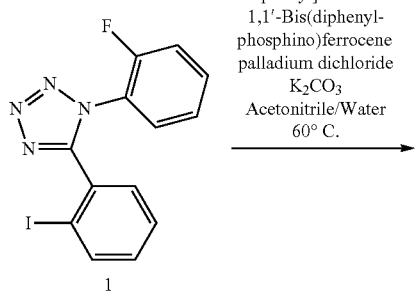

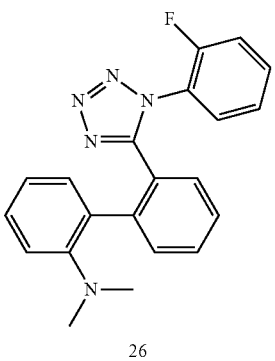

Compound 26 was prepared and isolated as its hydrochloride salt in 18% yield as an off-white solid (MP=139.8-141.7° C.; MH$^+$(found)=360.16183, MH$^+$(calc)=360.161903) from 1 in a similar fashion to Compound 2 using dimethyl[2-(4,4,5,5-tetramethyl-1,3,2-dioxaborolan-2-yl)-phenyl]amine.

Example 1.24

Process for Preparing 2-{2-[1-(2-Fluorophenyl)-1H-1,2,3,4-tetrazol-5-yl]phenyl}aniline (Compound 27)

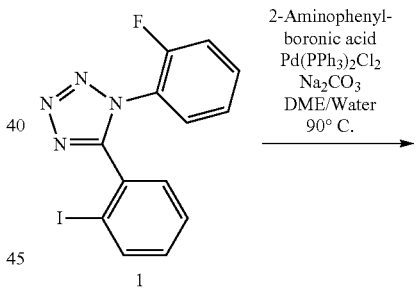

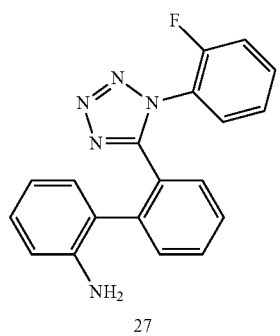

Compound 27 was prepared in 60% yield as a brown solid (MP=131.1-132.4° C.; MH$^+$(found)=332.13062, MH$^+$(calc)=332.130603) from 1 in a similar fashion to Compound 2 using 2-aminophenylboronic acid.

Example 1.25

Process for Preparing 1-(2-Fluorophenyl)-5-{2-[2-(methoxymethyl)phenyl]phenyl}-1H-1,2,3,4-tetrazole (Compound 29)

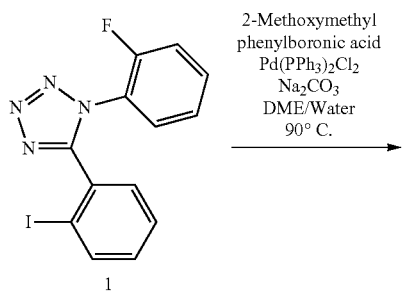

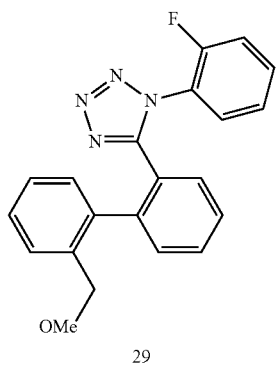

Compound 29 was prepared in 32% yield as a reddish-brown solid (MP=88.4-89.9° C.; MH⁺(found)=361.14571, MH⁺(calc)=361.145919) from 1 in a similar fashion to Compound 2 using 2-methoxymethylphenylboronic acid.

Example 1.26

Process for Preparing (2-{2-[1-(2-Fluorophenyl)-1H-1,2,3,4-tetrazol-5-yl]phenyl}phenyl)methanol (Compound 28)

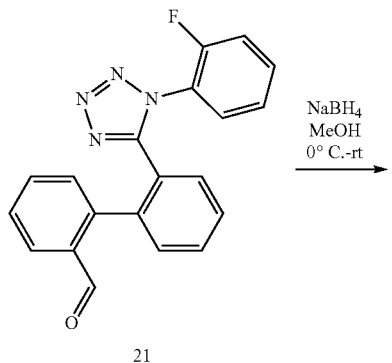

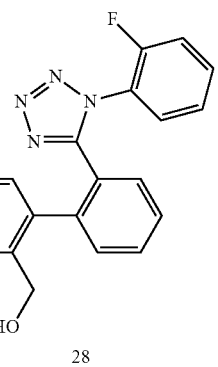

To a solution of 21 (200 mg) in methanol (10 ml) was added sodium borohydride (33 mg) at 0° C. After the completion of addition the reaction mixture was stirred with slow warming to room temperature. After 5 hours the reaction mixture was concentrated under reduced pressure to remove methanol. The residue was then diluted with water (25 ml), extracted with ethylacetate (100 ml*3) and the combined organic layers were washed with brine (50 ml), dried over anhydrous sodium sulphate, filtered and concentrated under reduced pressure to afford 210 mg of an off-white gum which was purified by column chromatography over silica gel (60-120 mesh, eluent: 20% ethylacetate in hexane) to afford the desired benzyl alcohol (28) as an off-white gum which solidified after prolonged drying in vacuo to an off-white solid (150 mg, 74%, MP=52.9-53.8° C. C; MH⁺(found)=347.13046, MH⁺(calc)=347.130269).

Example 1.27

Process for Preparing (E)-N-[(2-{2-[1-(2-Fluorophenyl)-1H-1,2,3,4-tetrazol-5-yl]phenyl}phenyl)methylidene]hydroxylamine (Compound 30)

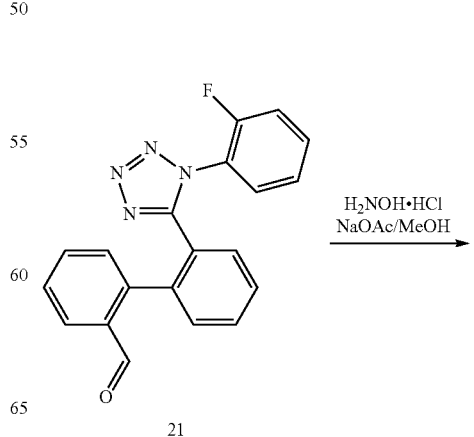

-continued

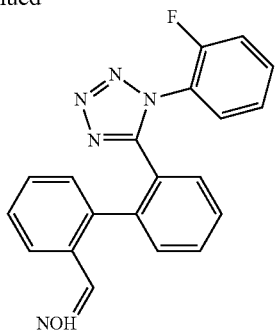

30

To a solution of (21) (150 mg) in methanol (6 ml) was added sodium acetate (43 mg) and hydroxylamine hydrochloride (37 mg) and the resultant reaction mixture was stirred at RT. After 8 hours the reaction mixture was concentrated to afford a brownish gummy liquid which was dissolved in water (50 mL) and extracted with ethylacetate (3*50 ml). The combined organic phases were washed with brine, dried over sodium sulphate, filtered and concentrated to afford the oxime (30) as an off white solid (150 mg, 96%; MH$^+$(found)=360.12598, MH$^+$(calc)=360.125518).

Example 1.28

Process for Preparing 2-{2-[1-(2-Fluorophenyl)-1H-1,2,3,4-tetrazol-5-yl]phenyl}benzonitrile (Compound 31)

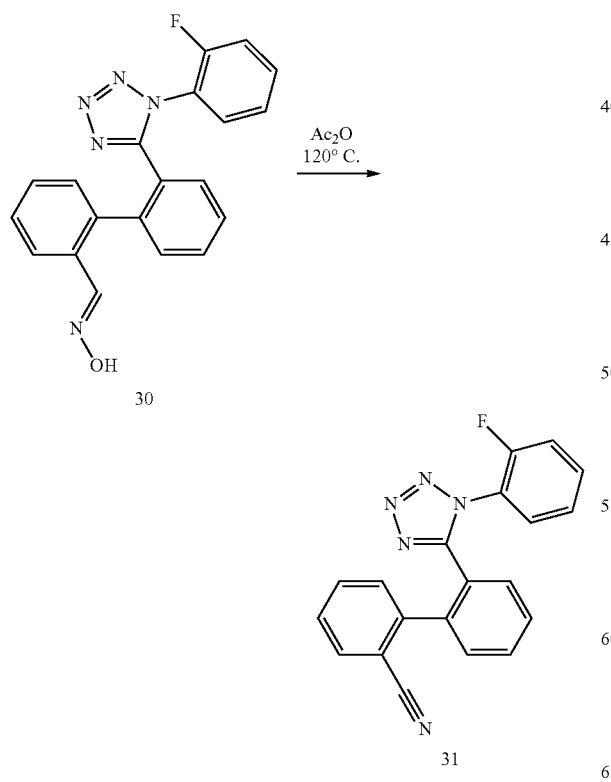

A solution of 21 (23 g) in acetic anhydride (425 mL) was heated for 18 hours at 120° C. in a sealed tube. Concentration provided a brown gummy liquid containing some corresponding aldehyde (cpd 21), which could best be removed by treatment of a solution of the crude product in THF/methanol with sodium borohydride (to convert aldehyde to the corresponding more polar benzylic alcohol (cpd 28)), standard extractive work up and chromatography (silica gel (60-120 mesh), eluent: 0.5% methanol in chloroform) to afford the nitrile 31 as an off-white solid (12 g, 52%; MP=161.9-163.8° C.; MH$^+$(found)=342.11504, MH$^+$(calc)=342.114953).

Example 1.29

Process for Preparing 5-{2-[2-(Difluoromethyl)phenyl]phenyl}-1-(2-fluorophenyl)-1H-1,2,3,4-tetrazole (Compound 32)

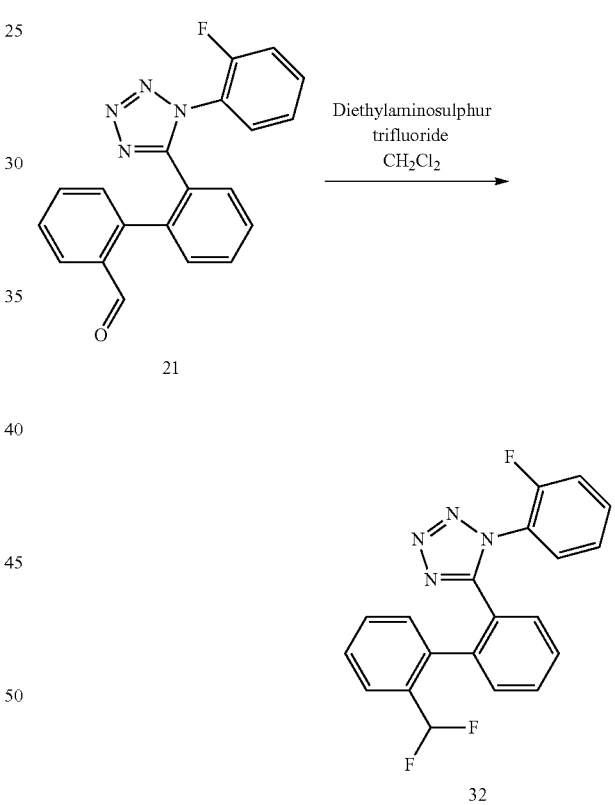

Diethylaminosulphur trifluoride (187 mg) was added dropwise at 0° C. to a solution of 21 (200 mg) in dichloromethane (10 ml). After addition the reaction mixture was allowed to warm at rt slowly and after 3 hours, it was diluted with water (30 ml), extracted with dichloromethane (50 ml*3), dried over anhydrous sodium sulphate, filtered and concentrated under reduced pressure to afford a yellow gum which was purified by column chromatography over silica gel (60-120 mesh, eluent: 8% ethyl acetate in hexane) to afford an off-white solid (65 mg, 31%; MP=120.2-121.4° C.; MH$^+$(found)=367.11656, MH$^+$(calc)=367.11651).

Example 1.30

Process for Preparing 5-{2-[2-(Fluoromethyl)phenyl]phenyl}-1-(2-fluorophenyl)-1H-1,2,3,4-tetrazole (Compound 33)

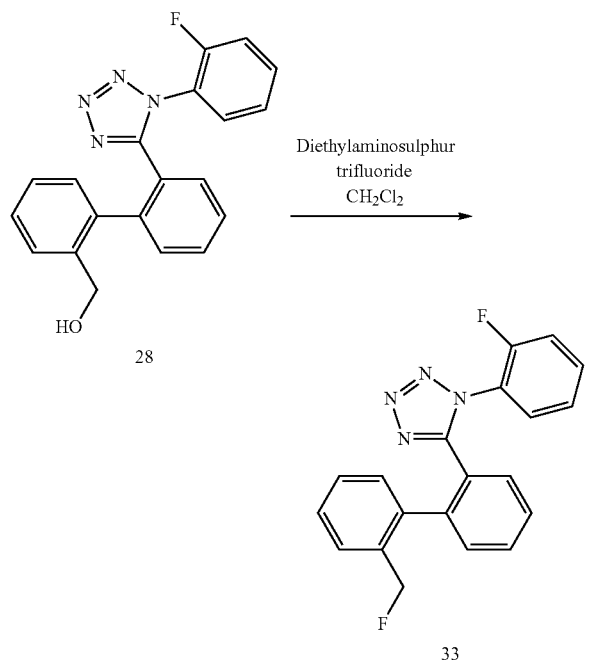

To a solution of 28 (220 mg) in dichloromethane (10 ml), was added diethylaminosulphur trifluoride (205 mg) at 0° C. After addition the reaction mixture was stirred with slow warming to room temperature and after 2 hours it was diluted with water (30 ml) and extracted with dichloromethane (75 ml*3). The combined organic layer washed with brine (25 ml), dried over anhydrous sodium sulphate, filtered and concentrated under reduced pressure to afford a yellowish gum which was purified by column chromatography over silica gel (60-120 mesh, eluent: 7% ethyl acetate in hexane) afford 33 as an off-white solid (41 mg, 18%; MP=67.0-68.4° C.; MH$^+$(found)=349.12555, MH$^+$(calc)=349.125932).

Example 1.31

Process for Preparing 2-{2-[1-(2-Fluorophenyl)-1H-1,2,3,4-tetrazol-5-yl]phenyl}-N-(2-methoxyethyl)aniline (Compound 42)

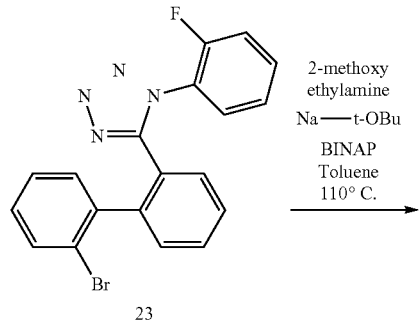

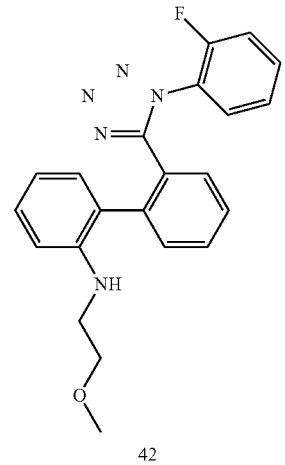

23 (300 mg), 2-methoxyethylamine (228 mg), sodium tert-butoxide (182 mg) and BINAP (24 mg) in toluene (10 ml) were mixed in a pressure tube. The mixture was purged with nitrogen for 5 minutes. Then tris(dibenzylidineacetone)dipalladium(0) (35 mg) was added under nitrogen. The vessel was tightly sealed and the reaction mixture was heated at 110° C. After 19 hours, the crude reaction mixture from a previous trial run of this reaction on a 50 mg scale was combined with the reaction mixture at hand and the combine mixture was concentrated. The obtained residue was diluted with water (10 ml) and extracted with dichloromethane (2*100 ml). The combined organic layer was washed with brine (20 ml), dried over sodium sulfate, filtered and concentrated to afford a black gummy material which was purified by flash column chromatography over silica gel (230-400 mesh, eluent: 0-6% ethyl acetate in hexane followed by methanol). The methanol eluent was further purified by preparative HPLC to provide 0.12 g of a colourless gum. A second purification by preparative HPLC gave an off-white solid (50 mg, 17%; MP=90.2-91.8° C.; MH$^+$found)=390.17297, MH$^+$(calc)=390.172468).

Example 1.32

Process for Preparing 1-(2-Chlorophenyl)-5-[2-(2-fluorophenyl)phenyl]-1H-1,2,3,4-tetrazole (Compound 48)

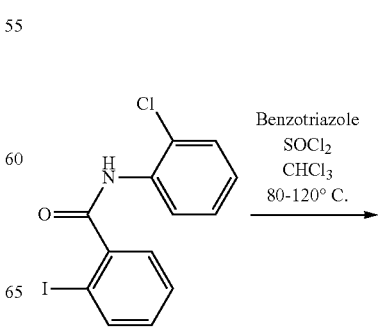

33
-continued

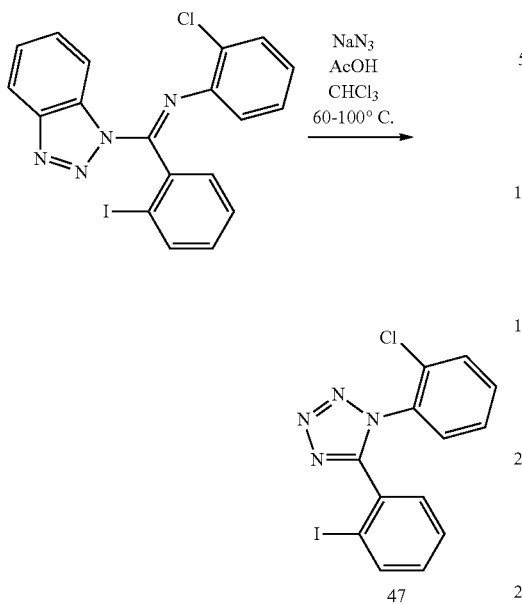

The intermediate 47 was prepared according to the above Scheme, in a similar fashion to intermediate 1.

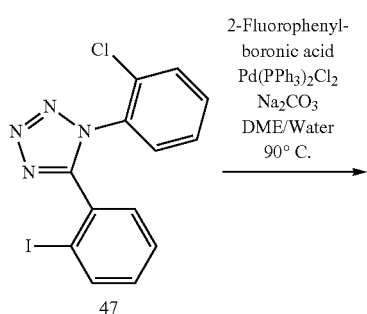

Compound 48 was prepared in 38% yield as a white solid (MP=117.8-119.2° C.; MH+(found)=351.08023, MH+(calc)=351.080732) from 47 in a similar fashion to Compound 25.

34

Example 1.33

Process for Preparing 1-(2-Chlorophenyl)-5-[2-(2-methoxyphenyl)phenyl]-1H-1,2,3,4-tetrazole (Compound 49)

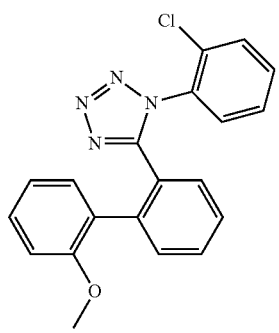

Compound 49 was prepared in 43% yield as a white solid (MP=112.2-113.3° C.; MH+(found)=363.10007, MH+(calc)=363.100719) from 47 in a similar fashion to Compound 13.

Example 1.34

Process for Preparing 1-(2-Methoxyphenyl)-5-[2-(2-methoxyphenyl)phenyl]-1H-1,2,3,4-tetrazole (Compound 51)

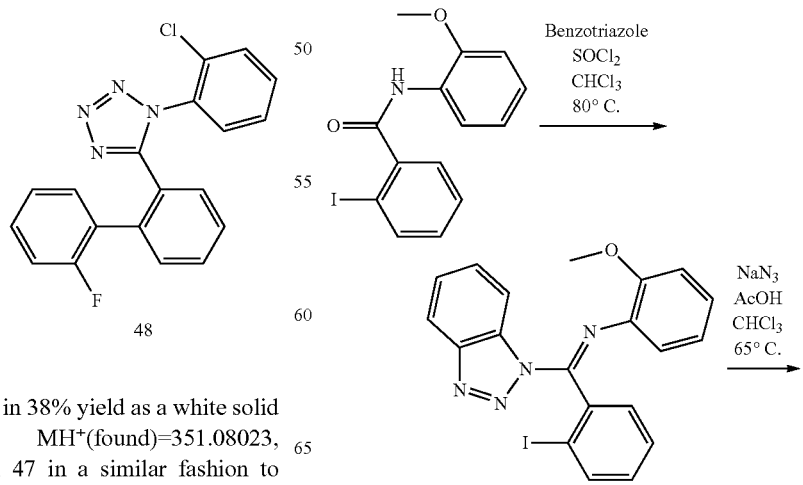

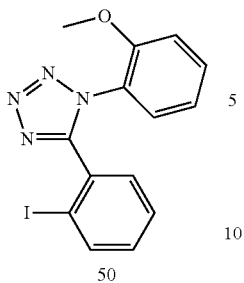

50

The intermediate 50 was prepared according to the above Scheme, in a similar fashion to intermediate 1

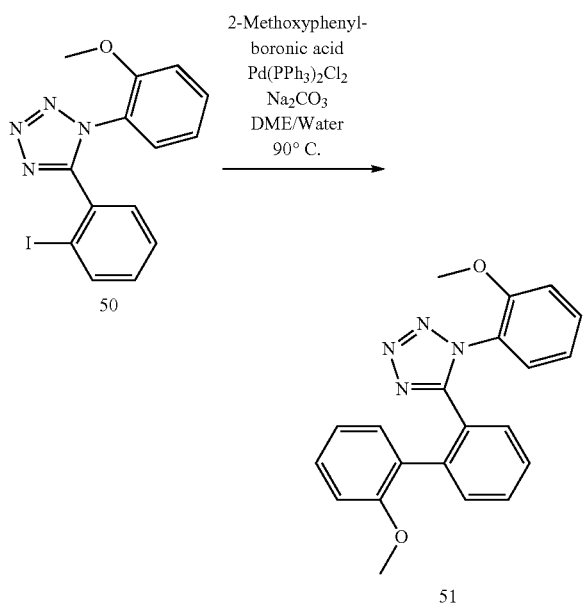

Compound 51 was prepared in 58% yield as a white solid (MP=149.6-150.9° C.; MH⁺(found)=359.15012, MH⁺(calc)=359.150256) from 50 in a similar fashion to Compound 13.

Example 1.35

Process for Preparing 2-{5-[2-(2-Methoxyphenyl)phenyl]-1H-1,2,3,4-tetrazol-1-yl}phenol (Compound 53)

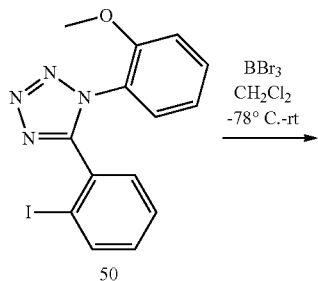

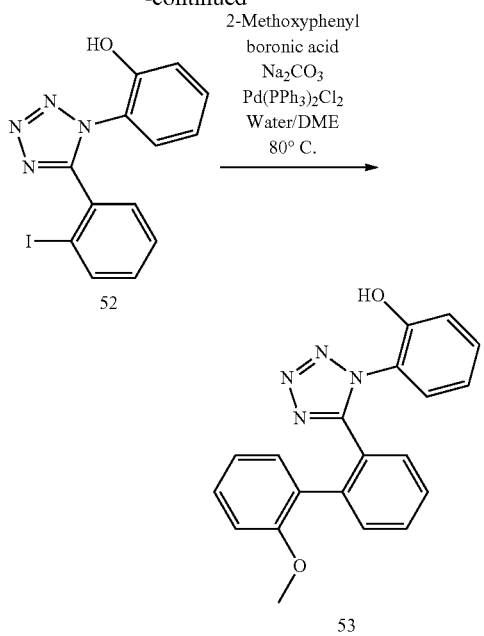

To a solution of 50 (700 mg) in dichloromethane (20 ml) was added boron tribromide (2.0 ml) at −78° C. After completion of addition the reaction mixture was stirred with slow warming to room temperature and after 2 hours it was cooled to −78° C., another 0.7 ml of boron tribromide was added and stirring continued with slow warming to rt. After 14 h methanol (20 ml) was added to the reaction mixture which was stirred for another 20 min at room temperature. Then the reaction mixture was concentrated under reduced pressure and the residue was quenched with saturated ammonium chloride solution (40 ml). The product was extracted with ethyl acetate (3*100 ml). The combined organic layer was washed with brine (50 ml), dried over anhydrous sodium sulfate, filtered and concentrated to afford a brownish solid which was purified by column chromatography using silica gel (230-400 mesh, eluent: 20% ethyl acetate in hexane) to afford intermediate 52 as white solid (0.60 g, 89%), which was used to prepare 53 in 39% yield as a white solid (MP=211.7-223.2° C.; MH⁺(found)=345.13495, MH⁺(calc)=345.134606) in a similar fashion to Compound 51.

Example 1.36

Process for Preparing 5-[2-(2-Fluorophenyl)phenyl]-1-(2-methoxyphenyl)-1H-1,2,3,4-tetrazole (Compound 54)

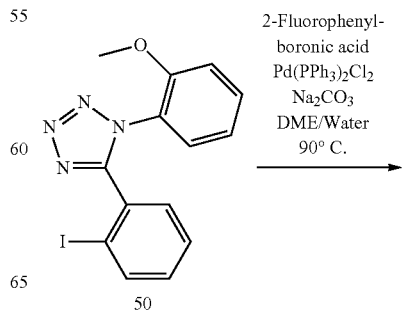

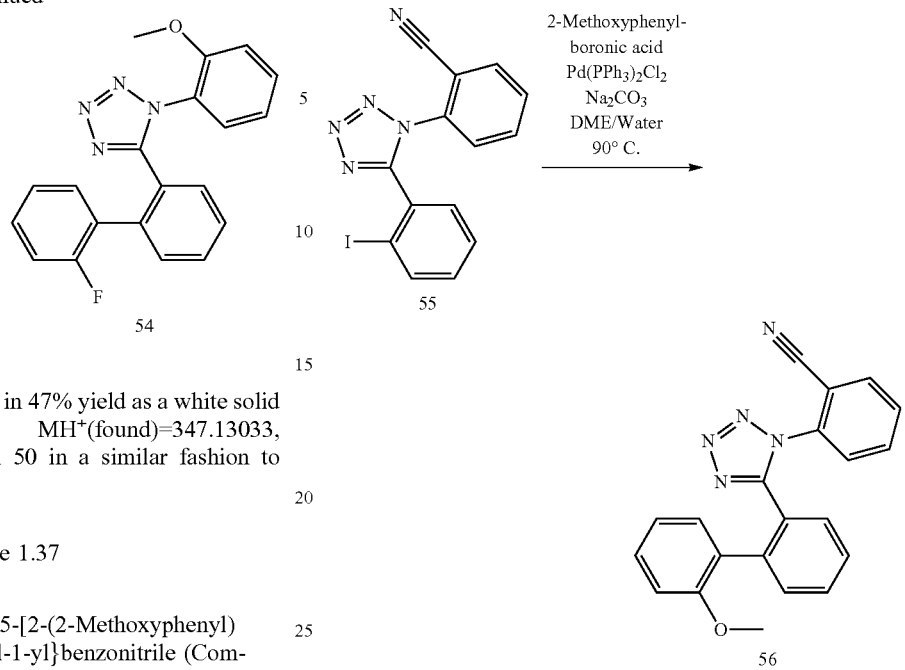

Compound 54 was prepared in 47% yield as a white solid (MP=133.6-134.9° C.; MH+(found)=347.13033, MH+(calc)=347.130269) from 50 in a similar fashion to Compound 25.

Example 1.37

Process for Preparing 2-{5-[2-(2-Methoxyphenyl)phenyl]-1H-1,2,3,4-tetrazol-1-yl}benzonitrile (Compound 56)

Compound 56 was prepared in 47% yield as an off-white solid (MP=162.4-163.9° C.; MH+(found)=354.13532, MH+(calc)=354.13494) from 55 in a similar fashion to Compound 13.

Example 1.38

Process for Preparing 1-[2-(Difluoromethoxy)phenyl]-5-[2-(2-fluorophenyl)phenyl]-1H-1,2,3,4-tetrazole (Compound 58)

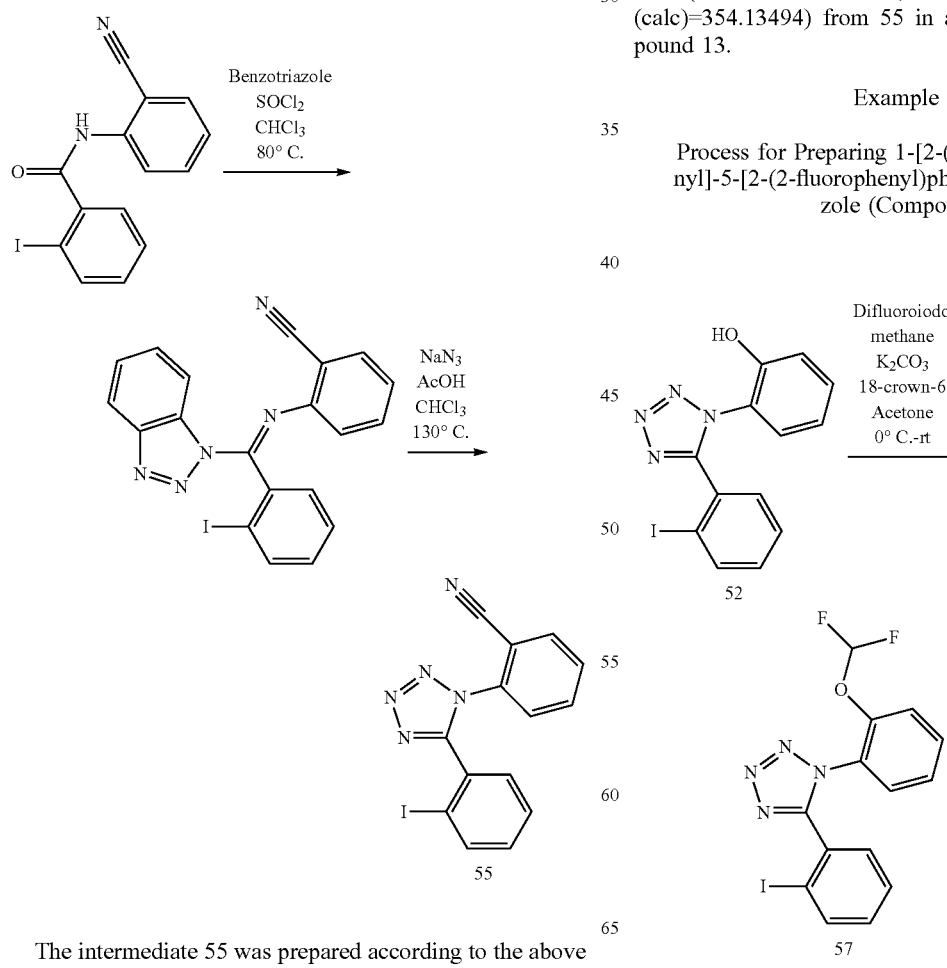

The intermediate 55 was prepared according to the above Scheme, in a similar fashion to intermediate 1.

-continued

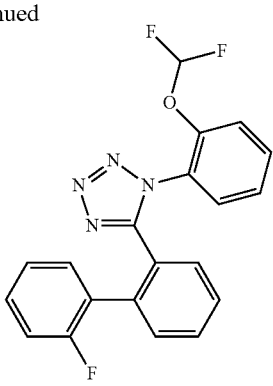

58

Compound 58 was prepared as a yellowish solid (MP=93.1-94.6° C.; MH+(found)=383.11142, MH+(calc)=383.111425) in two steps from 52 using the methodology used to make 5 from 2 followed by the methodology used to make Compound 25.

Example 1.39

Process for Preparing 1-[2-(Difluoromethoxy)phenyl]-5-[2-(2-methoxyphenyl)phenyl]-1H-1,2,3,4-tetrazole (Compound 59)

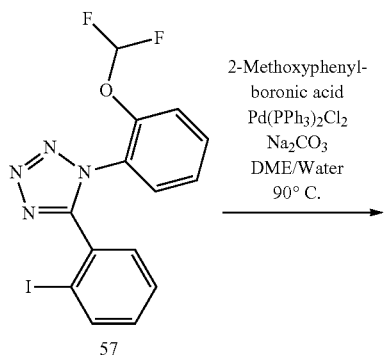

59

Compound 59 was prepared in 89% yield as an off-white solid (MP=130.1-131.8° C.; MH+(found)=395.13195, MH+(calc)=395.131412) from 57 in a similar fashion to Compound 13.

Example 1.40

Process for Preparing 2-(5-{2-[2-(Difluoromethoxy)phenyl]phenyl}-1H-1,2,3,4-tetrazol-1-yl)benzonitrile (Compound 62)

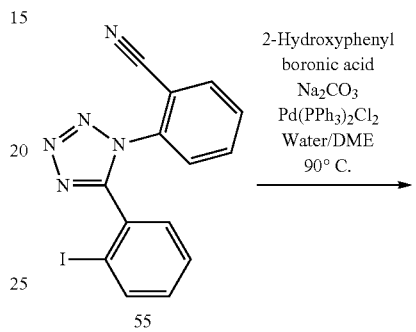

55

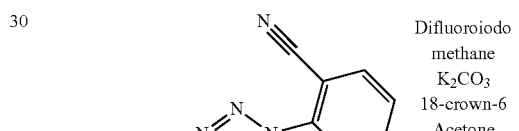

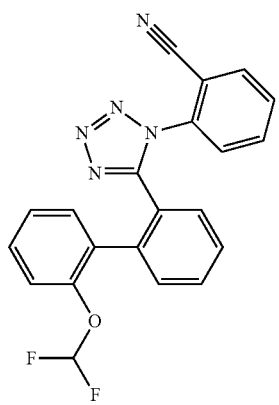

62

Compound 62 was prepared as an off-white solid (MP=138.1-140.8° C.; MH+(found)=390.11553, MH+(calc)=390.116096) in two steps from 55 using the methodology used to make 2 from 1 followed by the methodology used to make Compound 57 from 52.

Example 1.41

Process for Preparing 1-Phenyl-5-(2-phenylphenyl)-1H-1,2,3,4-tetrazole (Compound 65)

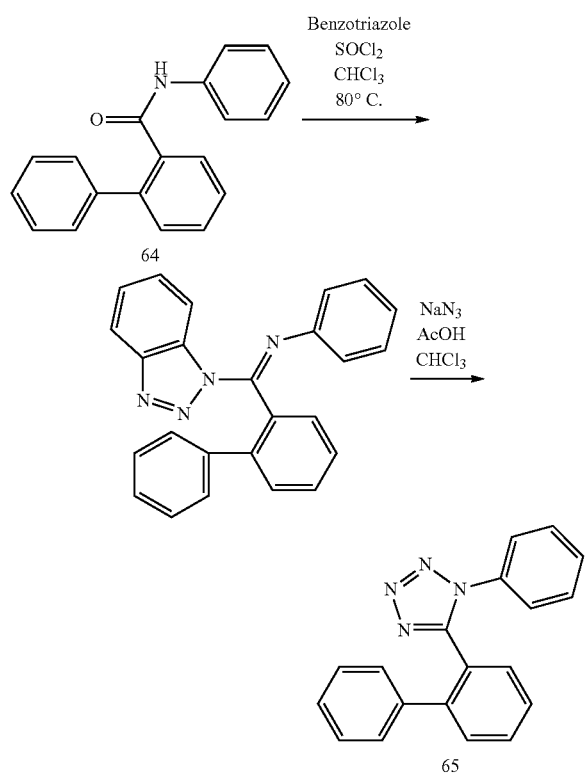

Compound 65 was prepared in two steps from 64 as an off-white solid (MP=125.3-126.2° C.; MH$^+$(found)=299.1309, MH$^+$(calc)=299.129671) in a similar fashion to Compound 1.

Example 2

Biological Activity of Compound According to the Present Invention—In Vitro Characterization of IK Inhibitors Following experiment determines the ability of a test compound to inhibit the activity of IK channels heterologously expressed in human HEK293 cells, and was used as the primary screen. The ability is determined as per cent inhibition of the activity induced by addition of the Ca$^{2+}$-ionophore A23187 (considered a maximum response). The activity is determined using a standard thallium (I) sensitive assay, e.g. using a fluorometric method in a Fluorescent Image Plate Reader (FLIPR) as described below in more detail.

Full concentration/response curves are generated and IC$_{50}$ values are calculated based on the degree of inhibition of the maximum response. IC$_{50}$ values (Inhibitory Concentration) represent the concentration of the test substance at which 50% of the maximum channel activity is inhibited.

Method

Human HEK293 cells over-expressing human IK are grown in culture medium (DMEM supplemented with 10% foetal bovine serum), in polystyrene culture flasks (175 mm$^2$) in a humidified atmosphere of 5% CO$_2$ in air, at 37° C. Cell confluence should be 80-90% on day of plating. Cells are rinsed with 4 mL of PBS (phosphate buffered saline) and incubated 2 min with 1 mL of Trypsin-EDTA. After addition of 25 mL of culture medium cells are re-suspended by trituration with a 25 mL pipette.

The cells are seeded at a density of ~3×10$^6$ cells/mL (25 µL/well) in black-walled, clear bottom, 384-well plates pre-treated with 0.01 g/L poly-D-lysin (20 µL/well for ≥30 min). Plated cells were allowed to proliferate for 24 h before loading with dye.

BTC-AM (50 mg, Invitrogen) is added 25.5 µl DMSO. The BTC-AM stock solution (2 mM) is diluted to a final concentration of 2 µM in Cl$^+$ free assay buffer (in mM: 140 Na$^+$-gluconate, 2.5 K$^+$-gluconate, 6 Ca2$^+$-gluconate, 1 Mg$^{2+}$ gluconate, 5 glucose, 10 HEPES, pH 7.3) containing 2 µM ouabain, 2 mM amaranth and 1 mM tartrazine.

The culture medium is aspirated from the wells, and 25 µl of the BTC-AM loading solution are added to each well. The cells are incubated at 37° C. for 60 min.

After the loading period, the Tl$^+$-sensitive BTC fluorescence signal is measured over time using a FLIPR.

Settings/Parameters

Temperature: Room temp.

First addition: 12 µl test or control compound after 15 sec at a rate of 30 µL/sec and starting height of 20 µL Second addition: 12 µL stimulus buffer (Cl$^-$ free assay buffer supplemented with 1 mM Tl$_2$SO$_4$, 5 µM A23187 as well as the quenchers amaranth (2 mM) and tartrazine (1 mM)) is added after an additional 3 minutes at a rate of 30 µL/sec and starting height of 30 µL Reading intervals: First sequence—3 sec×5, 2 sec×24 and 5 sec×25

Second sequence—1 sec×5, 2 sec×24 and 5 sec×36

Addition plates (compound plate and stimulus plate) are placed in positions 2 and 3, respectively. Cell plates are placed in position 1 and run using the "IK blocker (EtOH wash, two additions)" program. FLIPR will then take the appropriate measurements in accordance with the interval settings above. Fluorescence obtained after stimulation is corrected for the mean basal fluorescence (in Cl$^-$ free assay buffer).

Full concentration/response curves are generated and IC$_{50}$ values ("Inhibitory Concentration", i.e. the concentration of the test substance at which 50% of the maximum channel activity is inhibited) are calculated. The responses are calculated based on peak values.

Results

Biological activities of compounds according to the present invention are reported in Table 1 below.

TABLE 1

| Compound No. | IC50 (µM) |
|---|---|
| 2 | 5.9 |
| 3 | 0.037 |
| 4 | 0.03 |
| 5 | 0.29 |
| 6 | 0.71 |
| 7 | 0.016 |
| 8 | 0.59 |
| 9 | 0.77 |
| 12 | 0.3 |
| 13 | 0.11 |
| 14 | 0.46 |
| 15 | 1.7 |
| 16 | 0.19 |

TABLE 1-continued

| Compound No. | IC50 (μM) |
|---|---|
| 17 | 1 |
| 19 | 0.51 |
| 20 | 0.29 |
| 21 | 0.55 |
| 22 | 1.7 |
| 23 | 0.55 |
| 24 | 0.36 |
| 25 | 0.7 |
| 26 | 0.82 |
| 27 | 0.9 |
| 28 | 0.77 |
| 29 | 0.058 |
| 30 | 0.057 |
| 31 | 0.11 |
| 32 | 0.87 |
| 33 | 0.017 |
| 40 | 0.8 |
| 42 | 0.68 |
| 48 | 1 |
| 49 | 0.54 |
| 51 | 1.2 |
| 53 | 1.2 |
| 54 | 0.78 |
| 56 | 0.064 |
| 58 | 1.1 |
| 59 | 0.069 |
| 62 | 0.21 |
| 65 | 0.89 |

The invention claimed is:

1. A tetrazole of formula (I):

(I)

wherein
—X is hydrogen, halogen, hydroxy, cyano, $C_1$-$C_6$-alkyl, $C_1$-$C_6$-haloalkyl, $C_1$-$C_6$ alkoxy, or $C_1$-$C_6$ haloalkoxy; and
—Y is hydrogen, halogen, cyano, hydroxy, amino, carbamoyl, formyl, acetyl, $C_1$-$C_6$-alkyl, $C_1$-$C_6$-alkoxy, $C_1$-$C_6$-haloalkyl, $C_1$-$C_6$-haloalkoxy, $C_1$-$C_6$-cyanoalkyl, $C_1$-$C_6$-cyanoalkoxy, $C_1$-$C_6$-hydroxyalkyl, $C_1$-$C_6$-hydroxyalkoxy, $C_1$-$C_6$-thioalkoxy, $C_1$-$C_6$-alkylsulfinyl, $C_1$-$C_6$-alkylsulfonyl, $C_3$-$C_7$-cycloalkyl, $C_3$-$C_7$-cycloalkyl-C1-C6-alkoxy, $C_1$-$C_6$-alkoxy-$C_1$-$C_6$-alkoxy, $C_1$-$C_6$-alkoxy-carbonyl-$C_1$-$C_6$-alkoxy, acetyl-$C_1$-$C_6$-alkoxy, N,N-di-$C_1$-$C_6$-alkylamino, N(N,N-di-$C_1$-$C_6$-alkylamino)-$C_1$-$C_6$-alkyl-carbonyl-amino, N—($C_1C_6$-alkoxy-$C_1$-$C_6$-alkyl)-amino, N,N-di-$C_1$-$C_6$alkylamino-$C_1$-$C_6$alkoxy, N—$C_1C_6$-alkylsulfonyl-amino, N,N-di-$C_1C_6$-sulfonyl-amino, amino-carbonyl-$C_1$-$C_6$-alkoxy, hydroxylamine-$C_1$-$C_6$-alkylidene, benzyl, or benzamide;
or a stereoisomer thereof.

2. The compound according to claim 1, wherein X is hydrogen, halogen, hydroxy, cyano, $C_1$-$C_6$-alkoxy, or $C_1$-$C_6$-haloalkoxy.

3. The compound according to claim 2, wherein X is hydrogen, fluorine, chlorine, hydroxy, cyano, methoxy, fluoromethoxy, chloromethoxy, difluoromethoxy, or dichloromethoxy.

4. The compound according to claim 1, wherein Y is hydrogen, halogen, cyano, hydroxy, amino, carbamoyl, formyl, acetyl, $C_1$-$C_6$-alkyl, $C_1$-$C_6$-alkoxy, $C_1$-$C_6$-haloalkyl, $C_1$-$C_6$-haloalkoxy, $C_1$-$C_6$-cyanoalkoxy, $C_1$-$C_6$-hydroxyalkyl, $C_1$-$C_6$-thioalkoxy, $C_1$-$C_6$-alkylsulfinyl, $C_1$-$C_6$-alkylsulfonyl, $C_3$-$C_7$-cycloalkyl-$C_1$-$C_6$-alkoxy, $C_1$-$C_6$-alkoxy-$C_1$-$C_6$-alkoxy, $C_1$-$C_6$-alkoxy-carbonyl-$C_1$-$C_6$-alkoxy, acetyl-$C_1$-$C_6$-alkoxy, N,N-di-$C_1$-$C_6$-alkylamino, N—(N,N-di-$C_1$-$C_6$-alkylamino)-$C_1$-$C_6$-alkylamino, N—$C_1$-$C_6$-alkyl-carbonyl-amino, N—($C_1$-$C_6$-alkoxy- $C_1$-$C_6$-alkyl)-amino, N,N-di- $C_1$-$C_6$-alkylamino-$C_1$-$C_6$-alkoxy, N—$C_1$-$C_6$-alkylsulfonyl-amino, N,N-di-$C_1$-$C_6$-sulfonyl-amino, amino-carbonyl-$C_1$-$C_6$-alkoxy, hydroxylamine-$C_1$-$C_6$-alkylidene, benzyl, or benzamide.

5. The compound according to claim 4, wherein Y is halogen, cyano, amino, formyl, $C_1$-$C_6$-alkyl, $C_1$-$C_6$-alkoxy, $C_1$-$C_6$-haloalkyl, $C_1$-$C_6$-haloalkoxy, $C_1$-$C_6$-cyanoalkoxy, $C_1$-$C_6$-hydroxyalkyl, $C_1$-$C_6$-thioalkoxy, $C_3$-$C_7$-cycloalkyl-$C_1$-$C_6$-alkoxy, $C_1$-$C_6$-alkoxy-$C_1$-$C_6$-alkoxy, $C_1$-$C_6$-alkoxy-carbonyl-$C_1$-$C_6$-alkoxy, N,N-di-$C_1$-$C_6$-alkylamino, N—($C_1$-$C_6$-alkoxy-$C_1$-$C_6$-alkyl)-amino, amino-carbonyl-$C_1$-$C_6$-alkoxy, hydroxylamine-$C_1$-$C_6$-alkylidene benzamide.

6. The compound according to claim 5, wherein Y is fluorine, chlorine, cyano, amino, formyl, ethyl, methoxy, ethoxy, fluoromethoxy, difluoromethoxy, halomethoxy, cyanomethoxy, thiomethoxy, methoxy-ethoxy, hydroxylamine-methylidene, or benzamide.

7. The compound according to claim 1 that is:
   -2-{2-[1-(2-Fluorophenyl)-1H-1,2,3,4-tetrazol-5-yl]phenyl}phenol;
   -5-[2-(2-Ethoxyphenyl)phenyl]-1-(2-fluorophenyl)-1H-1,2,3,4-tetrazole;
   -1-(2-Fluorophenyl)-5-{2-[2-(2-methoxyethoxy)phenyl]phenyl}-1H-1,2,3,4-tetrazole;
   -5-{2-[2-(Difluoromethoxy)phenyl]phenyl}-1-(2-fluorophenyl)-1H-1,2,3,4-tetrazole;
   -1-(2-Fluorophenyl)-5-(2-phenylphenyl)-1H-1,2,3,4-tetrazole;
   -5-{2-[2-(Cyclopropylmethoxy)phenyl]phenyl}-1-(2-fluorophenyl)-1H-1,2,3,4-tetrazole;
   -2-(2-{2-[1-(2-Fluorophenyl)-1H -1,2,3 ,4-tetrazol-5-yl]phenyl}phenoxy)acetonitrile;
   -methyl 2-(2-{2-[1-(2-fluorophenyl)-1H-1,2,3,4-tetrazol-5-yl]phenyl}phenoxy)acetate;
   -1-(2-Fluorophenyl)-5-{2-[2-(propan-2-yloxy)phenyl]phenyl }-1H-1,2,3,4-tetrazole;
   -5-{2-[2-(Fluoromethoxy)phenyl]phenyl}-1-(2-fluorophenyl)-1H-1,2,3,4-tetrazole;
   -1-(2-Fluorophenyl)-5-[2-(2-methoxyphenyl)phenyl]-1H-1,2,3,4-tetrazole;
   -1-(2-Fluorophenyl)-5-{2-[2-(rnethylsulfanyl)phenyl]phenyl}-1H-1,2,3,4-tetrazole;
   -1-(2-Fluorophenyl)-5-{2-[2-(trifluoromethoxy)phenyl]phenyl}-1H-1,2,3,4-tetrazole;
   -1-(2-Fluorophenyl)-5-{2-[2-(rnethoxyrnethoxy)phenyl]phenyl}-1H-1,2,3,4-tetrazole;
   -2-(2-{2-[1-(2-Fluorophenyl)-1H-1,2,3,4-tetrazol-5-yl]phenyl}phenoxy)acetamide;
   -1-(2-Fluorophenyl)-5-[2-(2-methylphenyl)phenyl]-1H-1,2,3,4-tetrazole;
   -5 -[2-(2-Ethylphenyl)phenyl]-1 -(2-fluorophenyl)-1H-1,2,3 ,4-tetrazole;

-2-{2-[1-(2-Fluorophenyl)-1H-1,2,3,4-tetrazol-5-yl]phenyl}benzaldehyde;
-1-(2-Fluorophenyl)-5-{2-[2-(trifluoromethyl)phenyl]phenyl}-1H-1,2,3,4-tetrazole;
-5-[2-(2-Bromophenyl)phenyl]-1-(2-fluorophenyl)-1H-1,2,3,4-tetrazole;
-5-[2-(2-Chlorophenyl)phenyl]-1-(2-fluorophenyl)-1H-1,2,3,4-tetrazole;
-1-(2-Fluorophenyl)-5-[2-(2-fluorophenyl)phenyl]-1H-1,2,3,4-tetrazole;
-2-{2-[1-(2-Fluorophenyl)-1H-1,2,3,4-tetrazol-5-yl]phenyl}-N,N-dirnethylaniline;
-2-{2-[1-(2-Fluorophenyl)-1H-1,2,3,4-tetrazol-5-yl]phenyl}aniline;
1-(2-Fluorophenyl)-5-{2-[2-(rnethoxymethyl)phenyl]phenyl}-1H-1,2,3,4-tetrazole;
-(2-{2-[1-(2-Fluorophenyl)-1H-1,2,3,4-tetrazol-5-yl]phenyl}phenyl)methanol;
-(E)-N-[(2-{2-[1-(2-Fluorophenyl)-1H-1,2,3,4-tetrazol-5-yl]phenyl}phenyl)methylidene]hydroxylamine;
-2-{2-[1-(2-Fluorophenyl)-1H-1,2,3,4-tetrazol-5-yl]phenyl}benzonitrile;
-5-{2-[2-(Difluoromethyl)phenyl]phenyl}-1-(2-fluorophenyl)-1H-1,2,3,4-tetrazole;
-5-{2-[2-(Fluoromethyl)phenyl]phenyl}-1-(2-fluorophenyl)-1H-1,2,3,4-tetrazole;
-2-{2-[1-(2-Fluorophenyl)-1H-1,2,3,4-tetrazol-5-yl]phenyl}-N-(2-methoxyethyl)aniline;
1-(2-Chlorophenyl)-5-[2-(2-fluorophenyl)phenyl]-1H-1,2,3,4-tetrazole;
-1-(2-Chlorophenyl)-5-[2-(2-methoxyphenyl)phenyl]-1H-1,2,3,4-tetrazole;
-1-(2-Methoxyphenyl)-5-[2-(2-methoxyphenyl)phenyl]-1H-1,2,3,4-tetrazole;
-2-{5-[2-(2-Methoxyphenyl)phenyl]-1H-1,2,3,4-tetrazol-1-yl}phenol;
-5-[2-(2-Fluorophenyl)phenyl]-1-(2-methoxyphenyl)-1H-1,2,3,4-tetrazole;
-2-{5-[2-(2-Methoxyphenyl)phenyl]-1H-1,2,3,4-tetrazol-1-yl}benzonitrile;
-1-[2-(Difluoromethoxy)phenyl]-5-[2-(2-fluorophenyl)phenyl]-1H-1,2,3,4-tetrazole;
-1-[2-(Difluoromethoxy)phenyl]-5-[2-(2-rnethoxyphenyl)phenyl]-1H-1,2,3,4-tetrazole;
-2-(5-{2-[2-(Difluoromethoxy)phenyl]phenyl}-1H-1,2,3,4-tetrazol-1-yl)benzonitrile; or
-1-phenyl-5-(2-phenylphenyl)-1H-1,2,3,4-tetrazole.

8. A pharmaceutical composition comprising, as an active ingredient, a pharmaceutically effective amount of a compound according to claim 1.

* * * * *